US010590081B2

(12) United States Patent
Kim et al.

(10) Patent No.: US 10,590,081 B2
(45) Date of Patent: Mar. 17, 2020

(54) GUANIDINE COMPOUNDS AND USE THEREOF

(71) Applicant: ImmunoMet Therapeutics Inc., Houston, TX (US)

(72) Inventors: Sung Wuk Kim, Gyeonggi-do (KR); Hong Woo Kim, Daejeon (KR); Sang Hee Yoo, Daejeon (KR); Ji Sun Lee, Daejeon (KR); Hye Jin Heo, Daejeon (KR); Hong Bum Lee, Daejeon (KR); Ji Ae Kook, Daejeon (KR); Young Woo Lee, Daejeon (KR)

(73) Assignee: ImmunoMet Therapeutics Inc., Houston, TX (US)

( * ) Notice: Subject to any disclaimer, the term of this patent is extended or adjusted under 35 U.S.C. 154(b) by 0 days.

(21) Appl. No.: 15/569,584

(22) PCT Filed: Apr. 30, 2015

(86) PCT No.: PCT/KR2015/004423
§ 371 (c)(1),
(2) Date: Oct. 26, 2017

(87) PCT Pub. No.: WO2016/175357
PCT Pub. Date: Nov. 3, 2016

(65) Prior Publication Data
US 2018/0093953 A1 Apr. 5, 2018

(51) Int. Cl.
C07D 295/215 (2006.01)
C07D 211/38 (2006.01)
C07C 279/26 (2006.01)
C07D 221/20 (2006.01)
C07D 207/10 (2006.01)
C07D 277/04 (2006.01)
C07D 209/52 (2006.01)
A61K 31/155 (2006.01)
A61K 31/40 (2006.01)
A61K 45/06 (2006.01)
A61K 31/44 (2006.01)

(52) U.S. Cl.
CPC .......... *C07D 211/38* (2013.01); *A61K 31/155* (2013.01); *A61K 31/40* (2013.01); *A61K 31/44* (2013.01); *A61K 45/06* (2013.01); *C07C 279/26* (2013.01); *C07D 207/10* (2013.01); *C07D 209/52* (2013.01); *C07D 221/20* (2013.01); *C07D 277/04* (2013.01)

(58) Field of Classification Search
CPC .................................................. C07D 295/215
USPC ........................................ 548/569; 514/428
See application file for complete search history.

(56) References Cited

U.S. PATENT DOCUMENTS

| | | | | |
|---|---|---|---|---|
| 2,467,371 A | * | 4/1949 | Swinden | C07C 279/26 546/231 |
| 3,960,949 A | * | 6/1976 | Ahrens | C07C 279/26 564/233 |
| 9,321,742 B2 | * | 4/2016 | Kim | C07D 333/20 |
| 9,540,325 B2 | * | 1/2017 | Kim | C07D 205/04 |
| 2012/0283299 A1 | | 11/2012 | Kim et al. | |
| 2014/0179661 A1 | * | 6/2014 | Kim | C07D 333/20 514/210.01 |
| 2014/0348749 A1 | | 11/2014 | Birsoy et al. | |
| 2015/0126518 A1 | * | 5/2015 | Kim | C07D 495/04 514/252.12 |

FOREIGN PATENT DOCUMENTS

| | | |
|---|---|---|
| FR | 2362623 A2 | 3/1978 |
| JP | 2013-516461 A | 5/2013 |
| JP | 2014-524424 A | 9/2014 |
| WO | WO-95/20950 A1 | 8/1995 |
| WO | WO-02/074740 A1 | 9/2002 |
| WO | 2013/022280 * | 2/2013 |
| WO | WO-2013/022279 A2 | 2/2013 |
| WO | WO-2014/123364 A1 | 8/2014 |
| WO | WO-2016/080810 A2 | 5/2016 |

OTHER PUBLICATIONS

Yu et al., "Physical characterization of, etc.," PSTT, vol. 1(3), 118-127). (Year: 1998).*
Braga et al., "Making crystals from . . . " J. Royal Soc. Chem. Commun. p3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*
Ivanisevic et al. "Use of X-ray . . . " Pharm. Sci. Encycl. p. 1-42. (Year: 2010).*
Seddon "Pseudopolymorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Jordan "Tamoxifen . . . " Nature Rev. v.2, p. 205-213. (Year: 2003).*
Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*
Guillory (in Brittain ed.), "Polymorphism in Pharmaceutical Solids.," NY: Marcel Dekker, Inc., 1-2, 125-181, 183-226. (Year: 1999).*
Ettmayer et al., "Lessons Learned, etc.," J. Med. Chem., 47(10): 2393-2404. (Year: 2004).*
Stella, "Prodrugs as therapeutics", Expert Opin. Ther. Patents, 14(3): 277-280. (Year: 2004).*

(Continued)

*Primary Examiner* — Patricia L Morris
(74) *Attorney, Agent, or Firm* — Clark & Elbing LLP

(57) ABSTRACT

The present invention relates to guanidine compounds for inhibiting mitochondrial oxidative phosphorylation (OXPHOS) and use thereof. More specifically, the present invention relates to a pharmaceutical composition for preventing or treating a OXPHOS-related disease, particularly cancer by inhibiting mitochondrial oxidative phosphorylation and reprogramming cellular metabolism.

5 Claims, No Drawings

(56) References Cited

OTHER PUBLICATIONS

Testa, "Prodrug Research, etc.," Biochemical Pharmacology, 68:2097-2106 (Year: 2004).*
Wolff, ed., Burger's Medicinal Chemistry and Drug Discovery, 5th edition, NY: John Wiley & Sons, 1996, vol. 1, pp. 949-976.*
Bundgaard, Design of Prodrugs, Chapter 1, p. 1. (Year: 1985).*
Silverman, Prodrugs and Drug Delivery Systems, The Organic Chemistry of Drug Design and Drug Action, Chapter 8, pp. 352-400. (Year: 1992).*
Banker et al., Prodrugs, Modern Pharmaceutics, 3rd edition, Revised and Expanded, pp. 451 and 596. (Year: 1986).*
Yuki et al., "Thermodynamics, etc.," CA 100:103930. (Year: 1984).*
Detweiler et al., "Some Substiuted, etc.," JACS, 74, 1483-5. (Year: 1952).*
Extended European Search Report for European Patent Application No. 15890798.0, dated Aug. 24, 2018 (13 pages).
Tsitsa et al., "Synthesis, crystal structure and biological properties of a new series of lipophilic s-triazines, dihydrofolate reductase inhibitors," Eur J Med Chem. 28(2):149-158 (1993).
Sathunuru et al., "A Facile One Pot Synthesis of 2, 4-Diamino-6-substituted s-Triazine Derivatives," J. Heterocyclic Chem. 45:1673-8 (2008).
International Search Report for International Application No. PCT/KR2015/004423, dated Jan. 13, 2016 (5 pages).
Written Opinion of the International Searching Authority for International Application No. PCT/KR2015/004423, dated Jan. 13, 2016 (6 pages).
International Preliminary Report on Patentability for International Application No. PCT/KR2015/004423, dated Oct. 31, 2017 (7 pages).
Notice of Reasons for Rejection and English Translation for Japanese Patent Application No. 2017-555763, dated Dec. 18, 2018 (8 pages).
Notice of Reasons for Rejection and English Translation for Japanese Patent Application No. 2017-555763, dated Jul. 16, 2019 (10 pages).
Notice of Reasons for Rejection and English Translation for Japanese Patent Application No. 2017-555763, dated Oct. 21, 2019 (10 pages).
First Office Action and English Translation for Chinese Patent Application No. 2015800793966, dated Nov. 5, 2019 (23 pages).

* cited by examiner

GUANIDINE COMPOUNDS AND USE THEREOF

TECHNICAL FIELD

The present invention relates to guanidine compounds for inhibiting mitochondrial oxidative phosphorylation (OXPHOS) and use thereof more specifically, the present invention relates to a pharmaceutical composition for preventing or treating a disease associated with OXPHOS, particularly cancer by inhibiting mitochondrial oxidative phosphorylation and reprogramming cellular metabolism.

BACKGROUND ART

The cellular metabolism is essential to generate resources such as ATP and biomass for their growth. The metabolic pathway to generate ATP is glycolysis and OXPHOS in mitochondria. Normal cells generate ATP via OXPHOS in mitochondria since 38 ATP molecules are generated per glucose molecule. However fast growing cells use glycolysis to generate ATP and lactate is the final metabolite in the process. For a long time, the dependency on OXPHOS is thought to be determined by availability of oxygen because oxygen is the molecule that accepts electrons during OXPHOS. Recently, the studies have shown that oxygen is not the determinant for OXPHOS, but rather cellular demands for biomass and NADH/NADPH in fast growing cells actively choose to use glycolysis rather than OXPHOS. Cancer cells are the best example of transformed metabolism and uncontrolled proliferation. Dr. Otto Warburg in 1920s noticed the cancer cells mainly use glycolysis and produce high level of lactate. The highly glycolytic nature of cancer metabolism is currently named "Warburg effect". The glycolytic metabolic feature leads to a speculation that cancer cells might have dysfunctional mitochondria. Recent studies however showed the significance of OXPHOS in cancer cells, in particular, cancer stem cell-like population, migrating cancer cells, circulating cancer cells in metastasis.

Metformin is a biguanide used for the treatment of diabetes. It is known to be an OXPHOS inhibitor that has been clinically used for a long time. Several retrospective epidemiology studies pointed out that cancer incidence was lower in diabetic patients who were treated with metformin. The anticancer effect of metformin has been demonstrated in in vitro and in vivo models of breast, colon, prostate and lung cancer. The efficacy of metformin is limited by its weak potency and distribution due to the cationic property, therefore the dependency on Organic Cation Transporter 1 (OCT1) in order to enter cells. Many studies used a more potent biguanide and antidiabetic drug, phenformin to demonstrate the anticancer effect of OXPHOS inhibitor. Phenformin is more lipophilic than metformin and shows less dependency on OCT1 to enter cells. Several studies showed phenformin has activity of tumor growth inhibition and moreover prevent rising of cells resistant to targeted therapies (YuanP, Proc Natl Acad Sci. 2013, 110(45): pp 18226-18231). Phenformin was shown to inhibit the growth of slow growing cancer cells or JARID1B$^{high}$ cells that might be responsible for drug resistance and relapse of disease (RoeschA, Cancer Cell, 2013, 23(6), pp 811-825)

In the last decade, the main anticancer therapy was focused on development of inhibitors of oncogenes or signaling proteins such as kinases and growth factor receptors. The response rates were marginal in most cases. The initial responses by the best therapies apparently looked promising, but majority of patients relapsed with much more aggressive and drug resistant form of cancers. The true mechanism of relapse is still needed to be discovered, but multiple relapse mechanism have been reported such as secondary mutations on the same target or activation of different route of signaling pathway. The mechanism of phenformin in overcoming drug resistance is not still clear. The OXPHOS inhibition may prevent further reprogramming after reprogramming upon co-treatment with targeted therapy, therefore it may cause energy crisis or prevent growth of slow growing population depending on OXPHOS.

Metformin has limited efficacy and tissue distribution and phenformin has been withdrawn from the market due to fatal safety issues. Thus, the conventional biguanide used for diabetic treatment have limitations as an anticancer agent.

DISCLOSURE

Technical Problem

The present invention relates to guanidine compounds or pharmaceutically-acceptable salts thereof with an improved activity of inhibiting mitochondrial oxidative phosphorylation (OXPHOS) and reprogramming cellular metabolism.

Another embodiment of the present invention is to provide a pharmaceutical composition for preventing or treating a disease-associated with mitochondrial oxidative phosphorylation (OXPHOS) or a method of preventing or treating a disease-associated with mitochondrial oxidative phosphorylation (OXPHOS) including administering the compound of the present invention to a subject in need.

Further embodiment of the present invention is to provide an anti-cancer pharmaceutical composition comprising the guanidine compounds or pharmaceutically-acceptable salts thereof as active ingredient.

Technical Solution

To achieve the technical object, an embodiment of the present invention relates to the guanide compounds, pharmaceutically acceptable salts, pharmaceutically acceptable solvates and prodrug derivatives which have superior inhibitory effect on cancer cell growth, cancer metastasis and cancer reoccurrence to conventional drugs, even though smaller amount of the compounds are used.

In addition, an embodiment of the present invention relates to a use of the guanidine compounds for inhibiting mitochondrial oxidative phosphorylation (OXPHOS) or reprogramming cellular metabolism.

DETAILED DESCRIPTION OF THE INVENTION

Hereinafter, the present invention can be explained in more detail.

In another aspect, the present invention provides the compound selected from the group consisting of the guanidine compounds having Formula 1, pharmaceutically acceptable salts, pharmaceutically acceptable solvates and prodrug derivatives:

[Chemical formula 1]

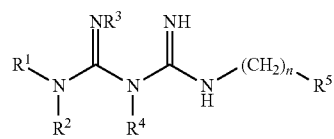

In the Chemical Formula 1, $R^1$ and $R^2$ are independently H, $C_1$-$C_6$ alkyl, or $C_1$-$C_6$ haloalkyl; or are taken together with N to which they are attached for forming 3 to 8-membered saturated or unsaturated heterocycloalkyl group, preferably 5-6 membered saturated or unsaturated heterocycloalkyl group, where the heterocycloalkyl ring may include optionally at least a heteroatom selected from the group consisting of N, O and S, and is substituted with at least a group selected from the group consisting of H, halogen, $C_1$-$C_4$ alkyl, $C_1$-$C_4$ haloalkyl, alkoxy, and $C_1$-$C_2$ alkylamino, $R^3$ and $R^4$ are independently H or $C_1$-$C_4$ alkyl, n is 0, 1 or 2, and $R^5$ is H, $C_3$-$C_7$ cycloalkyl, or aryl group represented by Chemical formula 2,

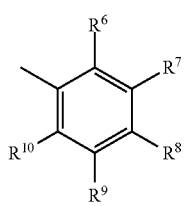

[Chemical Formula 2]

$R^6$, $R^7$, $R^8$, $R^9$ and $R^{10}$ are independently H, halogen, $C_1$-$C_4$ alkyl, $C_1$-$C_4$ alkoxy, $C_1$-$C_4$ halolalkyl, $C_1$-$C_4$ halolalkoxy, $SR^{11}$ or $OR^{12}$ where $R^{11}$ and $R^{12}$ are independently $C_1$-$C_3$ alkyl, $C_1$-$C_3$ haloalkyl, or $C_6$-$C_{10}$ aryl, or $R^6$, $R^7$, $R^8$, $R^9$ and $R^{10}$ are linked with an adjacent substituent to form of 5-6 membered saturated ring.

In Chemical formula 1, when $R^3$ and $R^4$ are hydrogen, the compound is represented by Chemical formula 3:

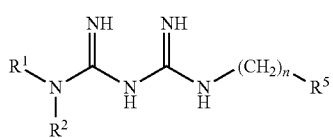

[Chemical formula 3]

$R^1$, $R^2$, $R^5$ and n are the same as defined in the Chemical formula 1.

In Chemical formula 1, when $R^3$ and $R^4$ are hydrogen and $R^5$ is aryl group represented by Chemical formula 3, the compound is represented by Chemical formula 4:

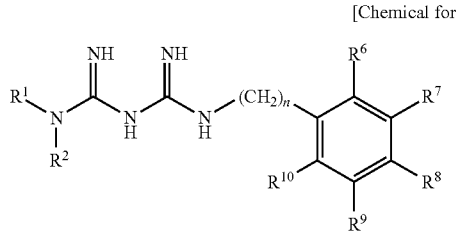

[Chemical formula 4]

$R^1$, $R^2$, $R^6$, $R^7$, $R^8$, $R^9$, $R^{10}$ and n are the same as defined in the Chemical formula 1.

In Chemical formulae 1, 3 and 4, the heterocycloalkyl in definition of $R^1$ and $R^2$ can be a 3 to 8-membered saturated heterocycloalkyl which may substituted with at least a group selected from the group consisting of H, halogen, $C_1$-$C_4$ alkyl, $C_1$-$C_4$ haloalkyl, $C_1$-$C_4$ alkoxy, and $C_1$-$C_2$ alkylamino, $R^3$ and $R^4$ are hydrogen, and $R^5$ is aryl group represented by Chemical formula 2 where $R^6$, $R^7$, $R^8$, $R^9$, and $R^{10}$ are the same as defined in the Chemical formula 1.

In an embodiment of the compounds represented by Chemical Formula 1, the substituents of $R^1$ and $R^2$ are taken together with N to which they are attached for forming 5 to 6-membered saturated or unsaturated heterocycloalkyl group and is substituted with halogen, $R^3$ and $R^4$ are independently H, n is 0, 1 or 2, and $R^5$ is aryl group represented by Chemical formula 2 where $R^6$, $R^7$, $R^8$, $R^9$, and $R^{10}$ are the same as defined in the Chemical formula 1 as described above.

In another embodiment of the compounds represented by Chemical Formula 1, $R^1$ and $R^2$ are taken together with N to which they are attached for forming 5 to 6 membered saturated or unsaturated heterocycloalkyl group and is substituted with halogen, $R^3$ and $R^4$ are independently H, n is 0, and $R^5$ is aryl group represented by Chemical formula 2 where $R^6$, $R^7$, $R^8$, $R^9$ and $R^{10}$ are $C_1$-$C_4$ halolalkoxy.

As used herein, the term "alkyl" refers to a saturated hydrocarbon group which is straight-chained or branched. Example groups include methyl, ethyl, propyl (n-propyl, isopropyl), tert-butyl, cyclopropylmethyl, cyclobutylmethyl, neopentyl and the like. The alkyl can be substituted with at least a halogen, such as F, Cl, Br or I and the example groups include $CF_3$, $CHF_2$, $CH_2F$, $CH_2Cl$, and the like.

As used herein, the terms "halo" or "halogen" includes fluoro, chloro, bromo, and iodo.

As used herein, the term "alkoxy" is meant to refer to a functional group containing an "alkyl" group bonded to an oxygen atom. An "alkyl" is defined above. As used herein, the term "haloalkoxy" is meant to refer to a functional group containing "haloalkyl" group bonded to an oxygen atom. An "alkyl" is defined above.

As used herein, the term "cycloalkyl" refers to non-aromatic carbocycles including cyclized alkyl, alkenyl, and alkynyl groups. Cyclolalkyl groups can include mono- or polycyclic ring systems, including spirocycles, or bridged cycles. Example cycloalkyl groups include cyclopropyl, cyclobutyl, cyclopentyl, cyclohexyl and cycloheptyl. $C_3$-$C_7$ cycloalkyl refers to a cycloalkyl radical containing from 3 to 7 ring carbon atoms. Examples of cycloalkyl groups include such groups as cyclopropyl, cyclobutyl, cyclopentyl, cyclohexl, cycloheptyl, cyclooctyl, pinenyl, and adamantanyl.

The term, "benzocycloalkyl" refers to moieties that have one or more aromatic rings fused to the cycloalkyl ring, and for examples, include benzo derivatives of cyclopentane and cyclohexane. The examples include indane, hydronaphthalene and tetrahydrohaphthalene. In Chemical formula 2, $R^6$, $R^7$, $R^8$, $R^9$ and $R^{10}$ are linked with an adjacent substituent to form of 5-6 membered saturated ring, so that the substituted of chemical formula 2 can be 9 to 10-membered benzocycloalkyl group.

As used herein, the term "heterocycloalkyl" refers to a non-aromatic heterocycle where one or more of the ring-forming atoms are heteroatom such as O, N, or S. The heterocyclolalkyl groups can include monocyclic, bicyclic or polycyclic ring systems, including spirocycles, or bridged cycles. Examples of heterocycloalkyl groups include pyrrolidinyl, pyrrolinyl, imidazolidinyl, imidazolinyl, pirazolidinyl, pirazolinyl, pyrazalinyl, piperidyl, piperazinyl, morpholinyl, thiazolidinyl, thiomorpholinyl, tetrahydrofuranyl, dithiolyl, oxathiolyl, dioxazolyl, oxathiazolyl, pyranyl, oxazinyl, oxathiazinyl, oxadiazinyl, azospiroheptane, azospirooctane, azabicyclohexane, and azabicyclohepane.

As used herein, the term "aryl" refers to a substituted or unsubstituted, mono- or bicyclic hydrocarbon aromatic ring system having 6 to 10 ring carbon atoms. Examples include unsubstituted or substituted phenyl and naphthyl groups.

In further aspect, the the present invention provides additional various compounds as well as the compounds having Chemical Formula 1, pharmaceutically acceptable salts, pharmaceutically acceptable solvates and prodrug derivatives. The examples of the present invention can include the following compounds:

N—(N-phenylcarbamimidoyl)-4,4-difluoropiperidine-1-carboximidamide
N—(N-(5,6,7,8-teterhydronaphthalene-2-yl)carbamimidoyl)-4,4-difluoropiperidine-1-carboximidamide
N—(N-(3,4-dichlorophenyl)carbamimidoyl)-4,4-difluoropiperidine-1-carboximidamide
N—(N-(2-bromophenyl)carbamimidoyl)-4,4-difluoropiperidine-1-carboximidamide
N—(N-(3-bromophenyl)carbamimidoyl)-4,4-difluoropiperidine-1-carboximidamide
N—(N-(4-bromophenyl)carbamimidoyl)-4,4-difluoropiperidine-1-carboximidamide
N—(N-(4-(trifluoromethoxy)phenyl)carbamimidoyl)-4-(dimethylamino)piperidine-1-carboximidamide
N—(N-(4-(methythio)phenyl)carbamimidoyl)-4',4-difluoropiperidine-1-carboximidamide
N—(N-(4-(trifluoromethythio)phenyl)carbamimidoyl)-4,4-difluoropiperidine-1-carboximidamide
N—(N-(4-isopropylphenyl)carbamimidoyl)-4,4-difluoropiperidine-1-carboximidamide
N—(N-(3-chloro-4-fluorophenyl)carbamimidoyl)-4,4-difluoropiperidine-1-carboximidamide
N—(N-(5,6,7,8-teterhydronaphthalen-1-yl)carbamimidoyl)-4,4-difluoropiperidine-1-carboximidamide
N—(N-(3-phenoxyphenyl)carbamimidoyl)-4,4-difluoropiperidine-1-carboximidamide
N—(N-(4-(trifluoromethylthio)phenyl)carbamimidoyl)thiazolidine-3-carboximidamide
N—(N-(3,4,5-trimethoxyphenyl)carbamimidoyl)-3,3-difluoropynolidine-1-carboximidamide
N—(N-(4-(trifluoromethoxy)phenyl)carbamimidoyl)-4-chloropiperidine-1-carboximidamide
N—(N-(4-(trifluoromethoxy)phenyl)carbamimidoyl)-4,4-difluoropiperidine-1-carboximidamide
N—(N-(3-chloro-4-iodophenyl)carbamimidoyl)-4,4-difluoropiperidine-1-carboximidamide
N—(N-(4-methoxyphenyl)carbamimidoyl)-4,4-difluoropiperidine-1-carboximidamide
N—(N-(3-methoxyphenyl)carbamimidoyl)-4,4-difluoropiperidine-1-carboximidamide
N—(N-(4-(trifluoromethyl)phenyl)carbamimidoyl)-4,4-difluoropiperidine-1-carboximidamide
N—(N-(3-bromo-4-iodophenyl)carbamimidoyl)-4,4-difluoropiperidine-1-carboximidamide
N—(N-(4-phenoxyphenyl)carbamimidoyl)-4,4-difluoropiperidine-1-carboximidamide
N—(N-(4-(trifluoromethoxy)carbamimidoyl)-4-ethoxypiperidine-1-carboximidamide
N-(N-(4-(trifluoromethoxy)phenyl)carbamimidoyl)-3,3-di fluoropyrrolidine-1-carboximidamide
N—(N-(3,4-dibromophenyl)carbamimidoyl)-4,4-difluoropiperidine-1-carboximidamide
N—(N-(3-fluoro-4-(trifluoromethoxy)phenyl)carbamimidoyl)-4,4-fluoropiperidine-1-carboximidamide
N—(N-(4-phenoxyphenyl)carbamimidoyl)-3,3-difluoropyrrolidine-1-carboximidamide
N—(N-(3-phenoxyphenyl)carbamimidoyl)-3,3-difluoropyrrolidine-1-carboximidamide
N—(N-(4-(trifluoromethyl)phenyl)carbamimidoyl)-3,3-difluoropyrrolidine-1-carboximidamide
N—(N-(3-chloro-4-iodophenyl)carbamimidoyl)-3,3-difluoropyrrolidine-1-carboximidamide
N—(N-(4-(trifluoromethylthio)phenyl)carbamimidoyl)-3,3-difluoropyrrolidine-1-carboximidamide
N—(N-(2-chlorophenyl)carbamimidoyl)-3,3-difluoropyrrolidine-1-carboximidamide
N—(N-(2-bromophenyl)carbamimidoyl)-3,3-difluoropyrrolidine-1-carboximidamide
N—(N-(2,4-dichlorophenyl)carbamimidoyl)-3,3-difluoropyrrolidine-1-carboximidamide
N—(N-(2-propylphenyl)carbamimidoyl)-3,3-difluoropyrrolidine-1-carboximidamide
N—(N-3,4-dimethoxyphenyl)carbamimidoyl)-3,3-difluoropyrrolidine-1-carboximidamide
N—(N-(3-chloro-4-(trifluoromethoxy)phenyl)carbamimidoyl)-3,3-difluoropyrrolidine-1-carboximidamide
N—(N-(3-bromo-4-(trifluoromethoxy)phenyl)carbamimidoyl)-3,3-difluoropyrrolidine-1-carboximidamide
N—(N-(2-bromobenzyl)carbamimidoyl)-4,4-difluoropiperidine-1-carboximidamide
N—(N-(4-(trifluoromethoxy)benzyl)carbamimidoyl)-4,4-difluoropiperidine-1-carboximidamide
N—(N-(3,4-dichlorobenzyl)carbamimidoyl)-4,4-difluoropiperidine-1-carboximidamide
N—(N-(4-trifluoromethyl)benzyl)carbamimidoyl)-3,3-difluoropyrrolidine-1-carboximidamide
N—(N-(3-trifluoromethyl)benzyl)carbamimidoyl)-3,3-difluoropyrrolidine-1-carboximidamide
N—(N-(3,4-dichloro)benzyl)carbamimidoyl)-3,3-difluoropyrrolidine-1-carboximidamide
N—(N-phenethylcarbamimidoyl)-3,3-difluoropyrrolidine-1-carboximidamide
N—(N-(4-bromophenethyl)carbamimidoyl)-3,3-difluoropyrrolidine-1-carboximidamide
N—(N-(cyclopropylmethypcarbamimidoyl)-4,4-difluoropiperidine-1-carboximidamide
N—(N-cyclopropylcarbamimidoyl)-4,4-difluoropiperidine-1-carboximidamide
N—(N-cyclohexylcarbamimidoyl)-4,4-difluoropiperidine-1-carboximidamide
N—(N-(cyclopropylmethyl)carbamimidoyl)-3,3-difluoropyrrolidine-1-carboximidamide
N—(N-(cyclopropylcarbamimidoyl)-3,3-difluoropyrrolidine-1-carboximidamide
N—(N-(cyclohexylcarbamimidoyl)-3,3-difluoropyrrolidine-1-carboximidamide
N—(N-(3-bromobenzyl)carbamimidoyl)-4,4-difluoropiperidine-1-carboximidamide
N—(N-(4-bromobenzyl)carbamimidoyl)-4,4-difluoropiperidine-1-carboximidamide
N—(N-(4-(trifluoromethoxy)phenyl)carbamimidoyl)-3,3-difluoropiperidine-1-carboximidamide
N—(N-(4-(trifluoromethoxy)phenyl)carbamimidoyl)thiazolidine-3-carboximidamide
N—(N-(4-(trifluoromethoxy)phenyl)carbamimidoyl)-N-2,2-2-trifluoroethylamino carboximidamide
N—(N-(4-(trifluoromethoxy)phenyl)carbamimidoyl)-4-(trifluoromethyl)piperidine-1-carboximidamide
N—(N-(4-(trifluoromethoxy)phenyl)carbamimidoyl)-N-1-cycloproylmethylamino carboximidamide N—(N-(4-(trifluoromethoxy)phenyl)carbamimidoyl)-3,4,4-trifluoropiperidine-1-carboximidamide N—(N-(4-(trifluoromethoxy)phenyl)carbamimidoyl)-4,4-difluoro-3-methylpiperidine-1-carboximidamide N—(N-(4-(trifluoromethoxy)phenyl)carbamimidoyl)-4-fluoropiperidine-1-carboximidamide N—(N-(4-(trifluoromethoxy)phenyl)carbamimidoyl)-(R)-3-fluoropyrrolidine-1-carboximidamide N—(N-(4-(trifluoromethoxy)phenyl)carbamimidoyl)-6-azaspiro[2.5]octane-6-carboximidamide N—(N-(4-(trifluoromethoxy)phenyl)carbamimidoyl)-3-azabicyclo[3.1.0]hexane-3-carboximidamide N-carbamimidoyl-3,3-difluoropyrrolidine-1-carboximidamide N-carbamimidoyl-4,4-difluoropiperidine-1-carboximidamide, and N-((4,4-difluoropiperidin-1-yl)(imino)methyl)-4,4-difluoropiperidine-1-carboximidamide The synthesis of certain compound represented by Chemical Formula 3 is illustrated in reaction scheme (1).

Reaction Scheme (1)

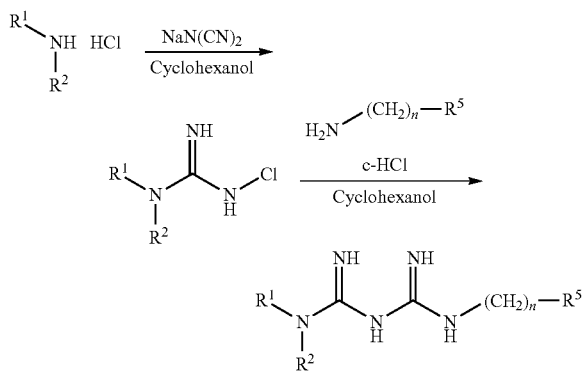

For example, the compound of example 17 was prepared as illustrated in reaction scheme 2. The detailed synthetic procedure is as described below.

Reaction Scheme (2)

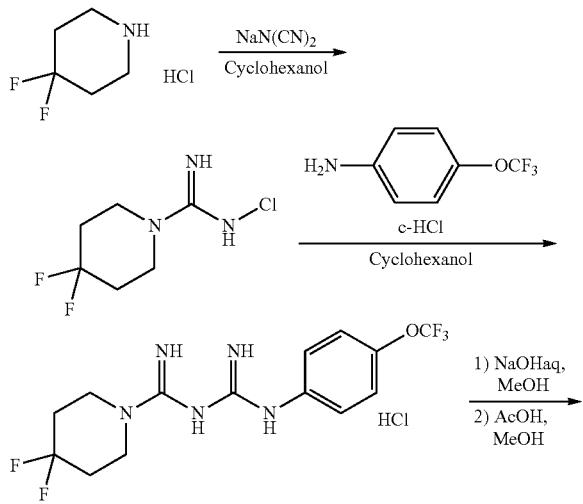

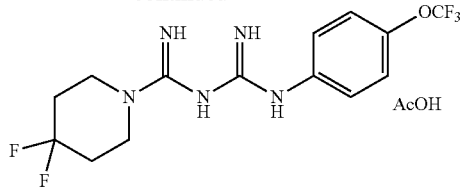

To the solution of 4,4-difluoropiperidine HCl (1.00 g, 6.34 mmol) in 30 mL cyclorohexanol was added sodium dicyanamide (0.62 g, 6.98 mmol). The reaction mixture was refluxed at 130 C for 2 h. The mixture was diluted with EtOAc and water. The separated organic layer was condensed under reduced pressure yielding yellow solid (0.89 g, 75.2%) residue followed by triturated with n-Hexanes. To the solution of the residue (0.5 g, 2.65 mmol) in 20 mL cyclohexanol were added conc. HCl solution (0.23 mL, 2.65 mmol) and 4-trifluoromethoxyaniline (0.35 mL, 2.65 mmol). The reaction mixture was refluxed at 130 C for 1 h. The mixture was cooled down to RT and stirred for 1 h further yielding the precipitate. The precipitate from the solution was filtered and re-dissolved in 10 mL MeOH. To the solution was added 0.5 mL 1.5 M NaOH resulting in precipitate. The solids were dissolved in 10 mL MeOH. To the solution was added acetic acid (0.23 mL, 3.98 mmol) and further stirred at RT for 1 h. The solvent was removed by a rotavapor yielding the desired white solids followed by being triturated with EtOAc (0.7 g, 56.3%).

The guanidine compounds of present invention can function as mitochondrial oxidative phosphorylation (OXPHOS) inhibitor. As used herein, the term "OXPHOS inhibitor" refers to an agent that inhibits oxidative phosphorylation, for example, oxidative phosphorylation in the mitochondria, either by direct inhibition of proteins involved in oxidative phosphorylation, or by inhibition of expression of the proteins involved in oxidative phosphorylation. The conventional OXPHOS inhibitors are metformin, phenformin and buformin. Metformin is a mitochondrial complex 1 inhibitor that can be used to target mitochondrial OXPHOS.

Thus, the present invention relates to a use of the guanidine compounds for inhibiting mitochondrial OXPHOS or reprogramming cellular metabolism. More specifically, the present invention relates to a pharmaceutical composition for preventing or treating a disease associated with mitochondrial OXPHOS.

The disease is at least one selected from the group consisting of diabetes mellitus, obesity, hyperlipemia, hypercholesterolemia, fatty liver, coronary artery disease, osteoporosis, polycystic ovary syndrome, metabolic syndrome, cancer, muscle pain, myocyte damage and rhabdomyolysis.

The diabetes mellitus is insulin-independent diabetes mellitus.

The cancer can be uterine cancer, breast cancer, gastric cancer, brain cancer, colorectal cancer, lung cancer, skin cancer, blood cancer and liver cancer, but not limited thereto.

The guanidine compounds of present invention have superior inhibitory effect on cancer cell growth, cancer metastasis and cancer reoccurrence to conventional drugs, even though smaller amount of the compounds are used.

The compounds of the present invention are improved guanide compounds with improved potency and anticancer activity in low glucose condition. The role of OXPHOS inhibitor of the present invention is not limited in growth inhibition of cancer, but also lower cancer stem cell like population, recurrence, and enhance efficacy of other anticancer drugs in the combination.

An aspect of the invention is to provide a method of preventing or treating a disease associated with OXPHOS, particularly cancer by inhibiting mitochondrial oxidative phosphorylation and reprogramming cellular metabolism, comprising administering the guanidine compound of present invention to a subject in need.

The compounds of invention can be used in combination with other pharmaceutical agents or treatment methods, for examples, chemotherapeutics, anti-cancer drugs, anti-cancer antibody drug, radiation, immunotherapy agents, and kinase inhibitors. The combination agent can be administered in a combined form or separate form.

Chemotherapeutic agents in combination with the compound of invention include (without limitation) alkylating agents, uracil mustards, chlormethine, cyclophosphamide (Cytoxan™), ifosfamide, melphalan, chlorambucil, pipobroman, triethlene-melamine, rtriethylenethiophosphoramine, busulfan, carmustine, lomustine, streptozocin, dacarbazine, temozolomide, methotrexate, 5-fluorouracil, floxuridine, cytarabine, 6-mercaptopurine, 6-thioguanide, gemcitabine, doxorubicin, epirubicin, idarubicin, ara-C, paclitaxel (Taxol™), navelbene, letrozole, anastrazole, capecitabine, cis-platin, carboplatin, and topoisomerase inhibitors. Anti-cancer antibodies include trastuzumab (Herceptin), and bevacizumab (Avastin). Immunotherapy agents include interferon, anti-PD1 antibody, anti-CTLA4 antibody, IDO1 inhibitors, and other immune cell therapies including adoptive T cell or NK cells. Kinase inhibitors include dasatinib, trametinib, palbociclib, or tyrosine kinase inhibitors such as erlotinib, gefatinib, but not limited thereto.

Measurement of Mitochondrial Complex I Inhibition

The electron transfer complex in mitochondria is composed of 5 complexes. The complex I accept electrons from NADH produced from glycolysis and TCA cycle and the electrons move to complex II, III and IV and the electron is finally transferred to $O_2$ and water molecule is generated. During the electron transfer, proton gradient is generated and the chemical gradient is a driving source to synthesize ATP at complex V. The mitochondrial inhibition of complex I indirectly assessed by measuring the oxygen consumption rate (OCR) at complex IV. When the mitochondrial ETC is inhibited, glycolysis is up-regulated and lactate production is increased. The solution outside of cells becomes acidic (lower pH) as lactate is transported to outside of cells. OCR and Extracellular acidification rate (ECAR) are determined by XF Analyzer (Seahorse Biosciences). The compounds of present invention caused lower OCR by inhibition of complex I. and higher ECAR by redirecting cellular metabolism to glycolysis.

Cytotoxicity Assay in Low Glucose Condition

The inhibition of oxidative phosphorylation (OXPHOS) is not cytotoxic to cells in normal glucose condition, because it is postulated that normal cells have compensatory mechanism under energy stress conditions such as low glucose. However OXPHOS inhibitors show cytotoxic effect on cells in the glucose deprived condition (BirsoyK, 2014). The glucose deprived condition is observed in tumor microenvironment potentially due to poor angiogenesis. Therefore the OXPHOS inhibitors may show anti-cancer effect on cancer cells in low glucose condition that may depict tumor microenvironment.

The compounds of the present invention were evaluated their cytotoxicity in SK-MEL-28, melanoma with 0.75 mM glucose supplement. The cytotoxic effect is compared with the cytotoxicity caused by phenformin. The cytotoxicity in low glucose condition is correlated with inhibition of oxygen consumption in mitochondria.

In Vivo Xenograft Study

The compounds of the present invention were evaluated in vivo using xenograft human cancer model in mice. The compounds of invention were administrated orally or interperitoneal injection. Tumor cell lines were cultured in vitro as monolayer culture. Using female BALB/c nude mice with immune system compromised, each mouse was inoculated subcutaneously at the right flank with tumor cells for tumor development. The treatment was started when the tumor size reaches approximately 100 $mm^3$ The pharmaceutically acceptable salt of the compound according to the present invention may be an acid addition salt formed using organic acid or inorganic acid. The organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, dichloroacetic acid, aminooxy acetic acid, benzenesulfonic acid, 4-toluenesulfonic acid and methanesulfonic acid salts. The inorganic acid may include, for examples, hydrochloric acid, hydrobromic acid, sulfuric acid, phosphoric acid, nitric acid, carbonic acid, and boric acid salts. The acid addition salt may be prepared by a common preparation method of salts, such as a) directly mixing the compound of the present invention and acid, b) dissolving the compound of the present invention or acid in a solvent or a an aqueous solvent and mixing them, or c) mixing the compound of the present invention and acid in a solvent or an aqueous solvent.

Thus, another embodiment of the present invention provides a pharmaceutical composition comprising the guanide compound or a pharmaceutical salt thereof as an active ingredient. The pharmaceutical composition according to the present invention has excellent cancer cell proliferation inhibition effect, and thus, it may be used as an anticancer agent for various cancers, and specific Examples of the cancer include breast, lung, melanoma, pancreas, brain, ovary, prostate, cervix, testes, renal, head and neck, liver, ymphoma, leukemia, endometrial cancer, cholangiocarcinoma, but not limited thereto.

The pharmaceutical composition of the present invention comprises at least one pharmaceutically acceptable carrier in addition to the active ingredient. As used herein, 'pharmaceutically acceptable carrier' means known pharmaceutical excipient that is useful for formulation of a pharmaceutically active compound for administration and is substantially non-toxic and non-sensitive under use conditions. The exact ratio of the excipient is determined by standard pharmaceutical practice, as well as by the solubility and the chemical properties of active compounds and the selected administration route.

The pharmaceutical composition of the present invention may be formulated into a form suitable for a desired administration method using adjuvant such as a physiologically acceptable excipient, a disintegrating agent, a sweetener, a binder, coating material, a blowing agent, a lubricant, a slip modifier, a flavoring agent and the like.

The pharmaceutical composition may be formulated in the form of tablets, capsules, pills, granule, powder, injections or liquid. The dosage form of the pharmaceutical composition and the pharmaceutically acceptable carrier may be appropriately selected according to technologies known in the art.

Meanwhile, as used herein, a 'subject' means a warm-blooded animal such as a mammal with a specific disease, disorder or condition, and for Example, it includes a human being, an orangutan, a chimpanzee, a mouse, a rat, a dog, a cow, a chicken, a pig, a goat, a sheep and the like, but is not limited thereto.

The term, 'treatment' or 'treating' includes relieving symptoms, temporarily or permanently removing the cause of symptoms, or preventing or slowing the appearance of symptoms and the progress of the disease, disorder or condition, but is not limited thereto.

The effective amount of the active ingredient of the pharmaceutical composition of the present invention means an amount required for achieving treatment of a disease. Thus, it may be controlled according to various factors including kind of disease, severity of disease, kind and content of active ingredients and other ingredients contained in the composition, kind of dosage form, and age, weight, general health state, gender and diet of a patient, administration time, administration route, secretion rate of the composition, treatment period, simultaneously used drugs, and the like. For example, in the case of an adult, the compound of the present invention may be administered once or several times a day in the total amount of 50 to 3000 mg/kg.

The guanide derivatives according to the present invention may exhibit excellent cancer cell proliferation inhibition and cancer metastasis and recurrence inhibition effects even with a small amount compared to the existing drugs, and thus, may be usefully used for treatment of various cancers including breast, lung, melanoma, pancreas, brain, ovary, prostate, cervix, testes, renal, head and neck, liver, lymphoma, leukemia, endometrial cancer, cholangiocarcinoma and the like, inhibition of cancer cell proliferation, and inhibition of cancer metastasis.

Advantageous Effect

The guanide derivatives according to the present invention may exhibit excellent cancer cell proliferation inhibition and cancer metastasis and recurrence inhibition effects even with a small amount compared to the existing drugs, and thus, may be usefully used for treatment of various cancers including breast, lung, melanoma, pancreas, brain, ovary, prostate, cervix, testes, renal, head and neck, liver, lymphoma, leukemia, endometrial cancer, cholangiocarcinoma and the like, inhibition of cancer cell proliferation, and inhibition of cancer metastasis.

EXAMPLE

Hereafter, the invention will be described in more detail through examples and comparative examples. However, the following examples are to merely illustrate the present invention, and the scope of the invention is not limited by them in any ways.

Example 1: N—(N-phenylcarbamimidoyl)-4,4-difluoropiperidine-1-carboximidamide hydrochloride

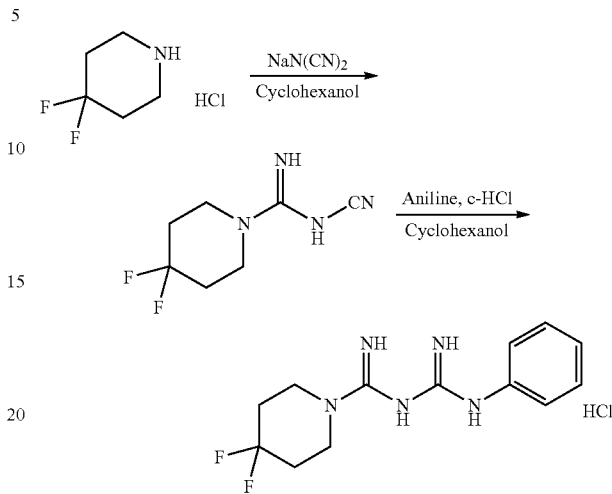

4,4-difluoropiperidine hydrochloride (1.0 g, 6.34 mmol) was dissolved in cyclohexanol (30 ml) at a room temperature and was added by sodium dicyanamide (0.62 g, 6.98 mmol). The solution was refluxed at 130° C. for 2 hours and cooled to a room temperature. By using ethylacetate and water, the aqueous layer was separated, dried under reduced pressure, and crystallized in a n-hexane to produce CN intermediate compound in a white solid (0.89 g, 75.2%). The CN intermediate compound (0.3 g, 1.59 mmol) was dissolved in cyclohexanol (10 ml) at a room temperature and was added by hydrochloride (0.14 ml, 1.59 mmol) and aniline (0.15 ml, 1.59 mmol). The solution was refluxed at 130° C. for 2 hours and cooled to a room temperature. The solution was agitated and the produced solid was filterated to obtain the title compound in white sold (0.46 g, 90.2%).

1H NMR (600 MHz, DMSO-d6) δ 10.04 (s, 1H), 7.95 (s, 2H), 7.37 (d, J=7.8 Hz, 2H), 7.31 (t, J=7.8 Hz, 2H), 7.24 (s, 2H), 7.05 (t, J=7.2 HZ, 1H), 3.60 (m, 4H), 2.08 (m, 4H) LCMS 382.1 [M+H]$^+$

Example 2. N—(N-(5,6,7,8-teterhydronaphthalene-2-yl)carbamimidoyl)-4,4-difluoro piperidine-1-carboximidamide hydrochloride

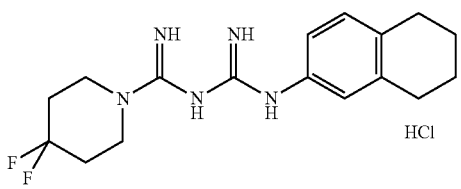 [SMILES: N=C(NC(=N)N1CCC(F)(F)CC1)Nc1ccc2c(c1)CCCC2 ; Cl]

The title compound (0.3 g, 52.5%) in white solid was obtained according to the same method of Example 1, except that 5,6,7,8-teterhydronaphthalene-2-amine was used.

1H NMR (600 MHz, DMSO-d6) δ 9.98 (s, 1H), 7.95 (s, 2H), 7.31 (s, 2H), 7.08 (d, J=7.8 Hz, 1H), 7.01 (s, 1H), 6.99 (d, J=7.8 Hz, 1H), 3.61 (m, 4H), 2.66 (m, 4H), 2.07 (m, 4H), 1.70 (m, 4H) LCMS 336.1 [M+H]$^+$

Example 3: N—(N-(3,4-dichlorophenyl)carbamimidoyl)-4,4-difluoropiperidine-1-carboximidamide hydrochloride

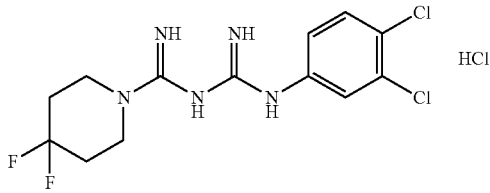 [SMILES: N=C(NC(=N)N1CCC(F)(F)CC1)Nc1ccc(Cl)c(Cl)c1 ; Cl]

The title compound (0.36 g, 58.1%) in white solid was obtained according to the same method of Example 1, except that 3,4-dichloroaniline was used.

1H NMR (600 MHz, DMSO-d6) δ 10.43 (s, 1H), 8.09 (s, 2H), 7.74 (d, J=2.4 Hz, 1H), 7.55 (d, J=9.0 HZ, 1H), 7.34 (d, J=9.0 Hz, 1H), 7.25 (s, 2H), 3.62 (m, 4H), 2.10 (m, 4H) LCMS 350.0, 352.0 [M+H]$^+$

Example 4. N—(N-(2-bromophenyl)carbamimidoyl)-4,4-difluoropiperidine-1-carboximidamide hydrochloride

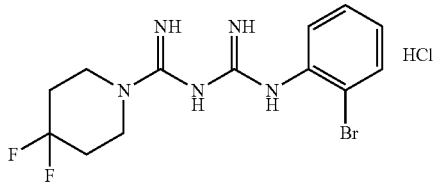 [SMILES: N=C(NC(=N)N1CCC(F)(F)CC1)Nc1ccccc1Br ; Cl]

The title compound (0.26 g, 61.9%) in white solid was obtained according to the same method of Example 1, except that 2-bromoaniline was used.

1H NMR (600 MHz, DMSO-d6) δ 9.02 (s, 1H), 7.89 (s, 1H), 7.65 (d, J=7.8 Hz, 1H), 7.60 (d, J=8.4 Hz, 1H), 7.39 (s, 2H), 7.35 (t, J=7.2 Hz, 2H), 7.11 (t, J=7.8 Hz, 1H), 3.55 (m, 4H), 2.04 (m, 4H) LCMS 360.0, 362.0 [M+H]$^+$

Example 5. N—(N-(3-bromophenyl)carbamimidoyl)-4,4-difluoropiperidine-1-carboximidamide hydrochloride

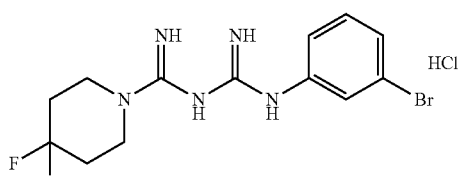

The title compound (0.33 g, 78.6%) in white solid was obtained according to the same method of Example 1, except that 3-bromoaniline was used.

1H NMR (600 MHz, DMSO-d6) δ 10.21 (s, 1H), 8.01 (s, 2H), 7.67 (s, 1H), 7.34 (d, J=7.8 Hz, 1H), 7.24 (t, J=8.4 Hz, 1H), 7.22 (s, 2H), 3.61 (m, 4H), 2.10 (m, 4H) LCMS 360.0, 362.0 [M+H]$^+$

Example 6. N—(N-(4-bromophenyl)carbamimidoyl)-4,4-difluoropiperidine-1-carboximidamide hydrochloride

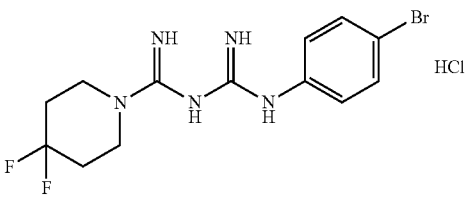 [SMILES: N=C(NC(=N)N1CCC(F)(F)CC1)Nc1ccc(Br)cc1 ; Cl]

The title compound (0.33 g, 78.6%) in white solid was obtained according to the same method of Example 1, except that 4-bromoaniline was used.

1H NMR (600 MHz, DMSO-d6) δ 10.35 (s, 1H), 8.08 (s, 2H), 7.48 (d, J=8.4 Hz, 2H), 7.37 (d, J=8.4 HZ, 2H), 7.31 (s, 4H), 3.63 (m, 4H), 2.11 (m, 4H) LCMS 360.0, 362.0 [M+H]$^+$

Example 7. N—(N-(4-(trifluoromethoxy)phenyl)carbamimidoyl)-4-(dimethylamino) piperidine-1-carboximidamide hydrochloride

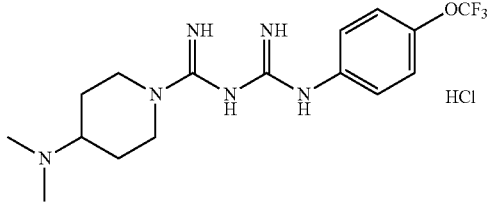 [SMILES: CN(C)C1CCN(C(=N)NC(=N)Nc2ccc(OC(F)(F)F)cc2)CC1 ; Cl]

The title compound (0.04 g, 11.0%) in white solid was obtained according to the same method of Example 1, except that N,N-dimethylpiperidine-4amine and 4-trifluoromethoxyaniline were used.

1H NMR (600 MHz, DMSO-d6) δ 10.31 (s, 1H), 7.93 (s, 2H), 7.50 (d, J=9.6 Hz, 2H)(, 7.31 (d, J=8.4 Hz, 2H), 7.18 (s, 2H), 4.45 (s, 1H), 4.19 (d, J=12.6 Hz, 1H), 3.43 (m, 1H), 2.97 (m, 1H), 2.68 (s, 6H), 2.15 (m, 2H), 1.72 (m, 2H) LCMS 373.1 [M+H]$^+$

Example 8. N—(N-(4-(methythio)phenyl)carbamimidoyl)-4,4-difluoropiperidine-1-carboximidamide hydrochloride

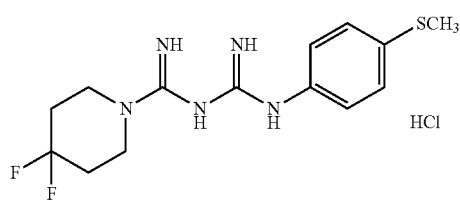 [SMILES: CSc1ccc(NC(=N)NC(=N)N2CCC(F)(F)CC2)cc1 ; Cl]

The title compound (0.39 g, 67.2%) in white solid was obtained according to the same method of Example 1, except that 4-methythioaniline was used.

1H NMR (600 MHz, DMSO-d6) δ 9.99 (s, 1H), 7.92 (s, 2H), 7.32 (d, J=8.4 Hz, 2H), 7.23 (d, J=8.4 Hz, 2H), 7.20 (s, 2H), 3.60 (m, 4H), 2.44 (s, 3H), 2.08 (m, 4H) LCMS 328.3 [M+H]+

Example 9. N—(N-(4-(trifluoromethythio)phenyl)carbamimidoyl)-4,4-difluoro piperidine-1-carboximidamide hydrochloride

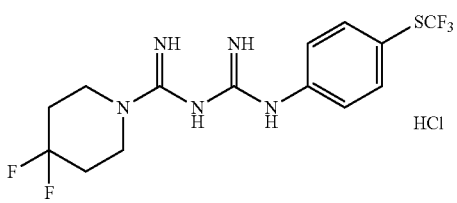

The title compound (0.38 g, 56.7%) in white solid was obtained according to the same method of Example 1, except that 4-trifluoromethythioaniline was used.
1H NMR (600 MHz, DMSO-d6) δ 10.35 (s, 1H), 8.06 (s, 2H), 7.62 (m, 2H), 7.56 (m, 2H), 7.23 (s, 2H), 3.61 (s, 4H), 2.10 (m, 4H) LCMS 382.3 [M+H]+

Example 10. N—(N-(4-isopropylphenyl)carbamimidoyl)-4,4-difluoropiperidine-1-carboximidamide hydrochloride

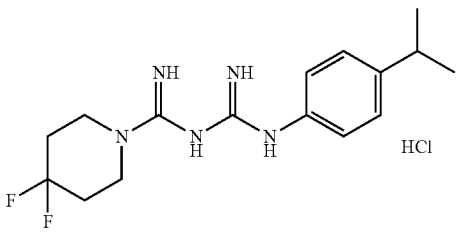 [SMILES: CC(C)c1ccc(NC(=N)NC(=N)N2CCC(F)(F)CC2)cc1 ; Cl]

The title compound (0.19 g, 33.3%) in white solid was obtained according to the same method of Example 1, except that 4-isopropylaniline was used.
1H NMR (600 MHz, DMSO-d6) δ 9.91 (s, 1H), 7.90 (s, 2H), 7.26 (m, 2H), 7.25 (s, 2H), 7.18 (m, 2H), 3.60 (m, 4H), 2.84 (m, 1H), 2.07 (m, 4H) 1.18 (d, J=7.2 Hz, 6H) LCMS 324.3 [M+H]+

Example 11. N—(N-(3-chloro-4-fluorophenyl)carbamimidoyl)-4,4-difluoropiperidine-1-carboximidamide hydrochloride

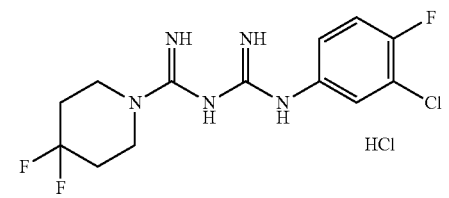 [SMILES: N=C(NC(=N)N1CCC(F)(F)CC1)Nc1ccc(F)c(Cl)c1 ; Cl]

The title compound (0.37 g, 62.7%) in white solid was obtained according to the same method of Example 1, except that 3-chloro-4-fluoroaniline was used.

1H NMR (600 MHz, DMSO-d6) δ 10.30 (s, 1H), 8.05 (s, 2H)), 7.66 (m, 1H), 7.36 (s, 2H), 7.32 (m, 1H), 7.30 (s, 2H), 3.61 (m, 4H), 1.99 (m, 4H) LCMS 334.1 [M+H]+

Example 12. N—(N-(5,6,7,8-teterhydronaphthalen-1-yl)carbamimidoyl)-4,4-difluoropiperidine-1-carboximidamide hydrochloride

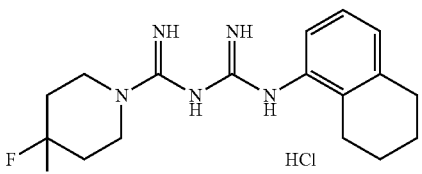

The title compound (0.34 g, 57.6%) in white solid was obtained according to the same method of Example 1, except 5,6,7,8-teterhydronaphthalene-1-amine was used.
1H NMR (600 MHz, DMSO-d6) δ 9.34 (s, 1H), 7.83 (s, 2H), 7.44 (s, 2H), 7.18 (d, J=7.8 HZ, 1H), 7.06 (t, J=7.8 Hz, 1H), 6.94 (d, J=7.8 Hz, 1H), 3.36 (m, 4H), 2.71 (m, 4H), 2.03 (m, 4H), 1.69 (m, 4H) LCMS 336.4 [M+H]+

Example 13. N—(N-(3-phenoxyphenyl)carbamimidoyl)-4,4-difluoropiperidine-1-carboximidamide hydrochloride

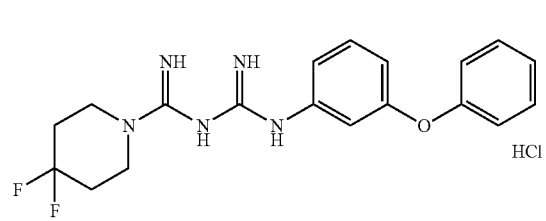 [SMILES: N=C(NC(=N)N1CCC(F)(F)CC1)Nc1cccc(Oc2ccccc2)c1 ; Cl]

The title compound (0.27 g, 61.3%) in white solid was obtained according to the same method of Example 1, except that 3-phenoxyaniline was used.
1H NMR (600 MHz, DMSO-d6) δ 10.10 (s, 1H), 7.91 (s, 2H), 7.42 (m, 2H), 7.27 (m, 1H), 7.25 (s, 1H), 7.18 (s, 2H), 7.15 (m, 1H), 7.13 (m, 1H), 7.07 (m, 1H), 7.00 (m, 2H), 3.56 (s, 4H), 2.03 (s, 4H) LCMS 374.1 [M+H]+

Example 14. N—(N-(4-(trifluoromethythio)phenyl)carbamimidoyl)thiazolidine-3-carboximidamide hydrochloride

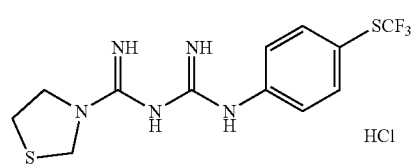

The title compound (0.14 g, 54.0%) in white solid was obtained according to the same method of Example 1, except that thiazolidine and 4-trifluoromethythioaniline was used.

1H NMR (600 MHz, DMSO-d6) δ 10.23 (brs, 0.5H), 7.92 (brs, 1H), 7.63 (m, 2H), 7.19 (m, 1H), 4.50 (s, 1H), 3.68 (m, 1H), 3.14 (m, 1H), 3.55 (m, 2H) LCMS 350.0 [M+H]+

Example 15. N—(N-(3,4,5-trimethoxyphenyl)carbamimidoyl)-3,3-difluoropyrrolidine-1-carboximidamide hydrochloride

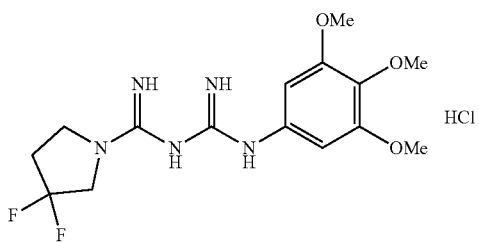 [SMILES: COc1cc(NC(=N)NC(=N)N2CCC(F)(F)C2)cc(OC)c1OC ; Cl]

The title compound (0.068 g, 10.0%) in white solid was obtained according to the same method of Example 1, except that 3,3-difluoropyrrolidine hydrochloride and 2,3,4-trimethoxyaniline were used.

1H NMR (600 MHz, DMSO-d6) δ 6.43 (brs, 2H), 3.76 (t, J=13.2 Hz, 2H), 3.71 (s, 3H), 3.59 (s, 3H), 3.55 (t, J=7.2 Hz, 2H), 2.44 (m, 2H), 1.76 (s, 3H) LCMS 358.2 [M+H]+

Example 16. N—(N-(4-(trifluoromethoxy)phenyl)carbamimidoyl)-4-chloropiperidine-1-carboximidamide hydrochloride

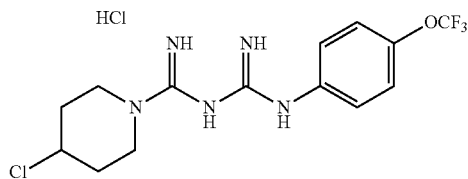 [SMILES: Cl ; N=C(NC(=N)N1CCC(Cl)CC1)Nc1ccc(OC(F)(F)F)cc1]

The title compound (610 mg, 100%) in white solid was obtained according to the same method of Example 1, except that 4-chloropiperidine and 4-trifluoromethoxyaniline was used.

1H NMR (600 MHz, DMSO-d6) δ 7.79 (m, 1H), 7.46 (d, J=9.0 Hz, 1H), 7.29 (m, 1H), 7.22 (m, 1H), 4.45 (m, 1H), 3.71 (m, 2H), 3.38 (m, 2H), 2.10 (m, 2H), 1.79 (m, 2H) LCMS 364.1 [M+H]+

Example 17. N—(N-(4-(trifluoromethoxy)phenyl)carbamimidoyl)-4,4-difluoropiperidine-1-carboximidamide acetate

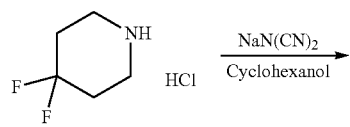

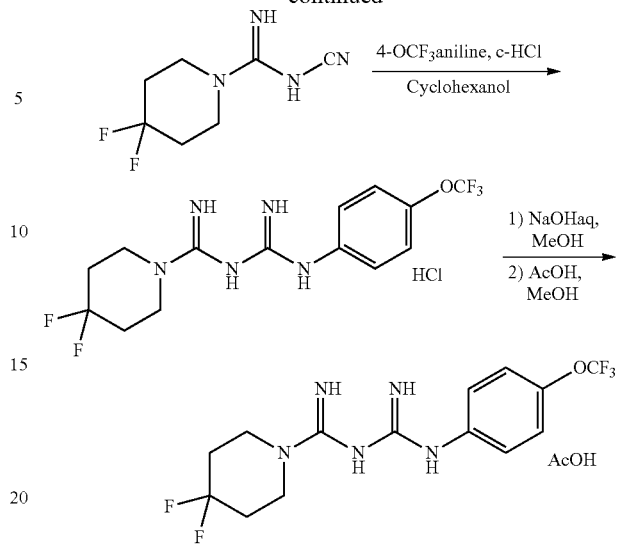

4,4-dichloropiperidine hydrochloride (1.0 g, 6.34 mmol) was dissolved in cyclohexanol (30 ml) at a room temperature and added by sodium dicyanamide (0.62 g, 6.98 mmol). The solution was refluxed at 130° C. for 2 hours and cooled to a room temperature. By using ethylacetate and water, the aqueous layer was separated, dried under reduced pressure, and crystallized in a n-hexane to produce CN intermediate compound in a white solid (0.89 g, 75.2%). The CN intermediate compound (0.5 g, 2.65 mmol) was dissolved in cyclohexanol (20 ml) at a room temperature and was added by hydrochloride (0.23 ml, 2.65 mol) and 4-trifluoromethoxyaniline (0.35 ml, 2.65 mmol). The solution was refluxed at 130° C. for 1 hour and cooled to a room temperature. The produced solid was filterated, dissolved in methanol (10 ml) and agitated for 1 hour with addition of 1.5 M NaOH (0.5 ml). The produced solid was filterated, dissolved in methanol (10 ml) and agitated for 1 hour at a room temperature with addition of acetic acid solution (0.23 ml, 3.98 mmol). The reaction solution was distilled under vacuum and crystallized in ethylacetate to produce the title compound in white solid (0.7 g, 56.3%).

1H NMR (600 MHz, DMSO-d6) δ 7.31 (s, 2H), 7.22 (d, J=9.0 Hz, 2H), 3.58 (m, 4H), 2.00 (m, 4H), 175 (s, 3H)

LCMS 366.1 [M+H]+

Example 18. N—(N-(3-chloro-4-iodophenyl)carbamimidoyl)-4,4-difluoropiperidine-1-carboximidamide acetate

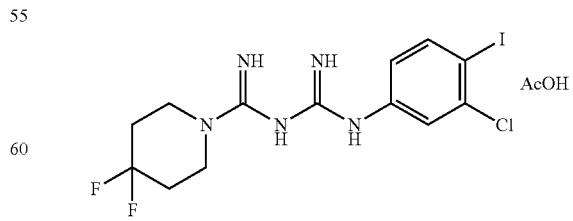

The title compound (0.10 g, 19.6%) in white solid was obtained according to the same method of Example 17, except that 3-chloro-4-iodoaniline was used.

1H NMR (600 MHz, DMSO-d6) δ 10.52 (s, 1H), 8.08 (s, 2H), 7.81 (d, J=8.4 Hz, 1H), 7.71 (d, J=2.4 Hz, 1H), 7.29 (s, 2H), 7.10 (dd, J=8.4 Hz, 2.4 Hz, 1H), 3.62 (s, 4H), 1.90 (s, 4H) LCMS 442.0 [M+H]⁺

Example 19. N—(N-(4-methoxyphenyl)carbamimidoyl)-4,4-difluoropiperidine-1-carboximidamide acetate

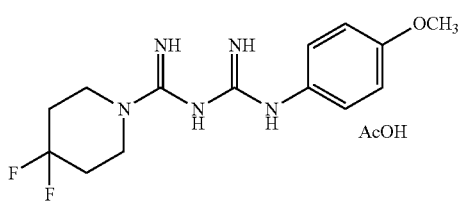 [SMILES: "AcOH" ; COc1ccc(NC(=N)NC(=N)N2CCC(F)(F)CC2)cc1]

The title compound (0.46 g, 77.9%) in white solid was obtained according to the same method of Example 17, except that 4-methoxyaniline was used.

1H NMR (600 MHz, DMSO-d6) δ 7.17 (s, 2H), 6.81 (m, 2H), 3.54 (s, 4H), 1.98 (s, 4H), 1.71 (s, 3H) LCMS 312.2 [M+H]⁺

Example 20. N—(N-(3-methoxyphenyl)carbamimidoyl)-4,4-difluoropiperidine-1-carboximidamide acetate

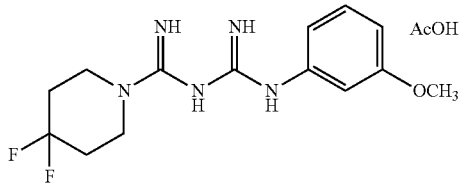 [SMILES: "AcOH" ; COc1cccc(NC(=N)NC(=N)N2CCC(F)(F)CC2)c1]

The title compound (0.36 g, 61.0%) in white solid was obtained according to the same method of Example 17, except that 3-methoxyaniline was used.

1H NMR (600 MHz, DMSO-d6) δ 7.13 (t, J=8.4 Hz, 1H), 6.90 (s, 1H), 6.81 (d, J=7.2 Hz, 1H), 6.54 (dd, J=8.4 Hz, 1H), 3.57 (m, 4H), 2.01 (m, 4H), 1.73 (s, 3H) LCMS 312.2 [M+H]⁺

Example 21. N—(N-(4-(trifluoromethyl)phenyl)carbamimidoyl)-4,4-difluoropiperidine-1-carboximidamide acetate

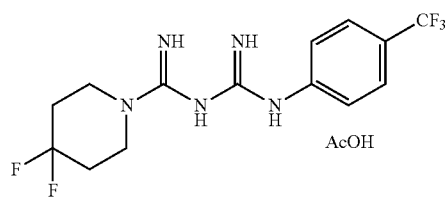 [SMILES: "AcOH" ; N=C(NC(=N)N1CCC(F)(F)CC1)Nc1ccc(C(F)(F)F)cc1]

The title compound (0.35 g, 53.8%) in white solid was obtained according to the same method of Example 17, except that 4-trifluoromethylaniline was used.

1H NMR (600 MHz, DMSO-d6) δ 7.57 (d, J=8.4 Hz, 2H), 7.49 (d, J=7.2 Hz, 2H), 3.60 (m, 4H), 2.04 (m, 4H), 1.76 (s, 3H) LCMS 350.2 [M+H]⁺

Example 22. N—(N-(3-bromo-4-iodophenyl)carbamimidoyl)-4,4-difluoropiperidine-1-carboximidamide acetate

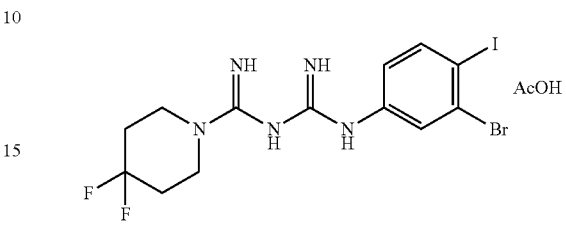

The title compound (0.30 g, 34.4%) in white solid was obtained according to the same method of Example 17, except that 3-bromo-4-iodoaniline was used.

1H NMR (600 MHz, DMSO-d6) δ 7.74 (d, J=8.4 Ha, 1H), 7.68 (s, 1H), 7.03 (d, J=7.2 Hz, 1H), 3.59 (m, 4H), 2.50 (m, 4H), 1.76 (s, 3H) LCMS 487.0, 488.0 [M+H]⁺

Example 23. N—(N-(4-phenoxyphenyl)carbamimidoyl)-4,4-difluoropiperidine-1-carboximidamide acetate

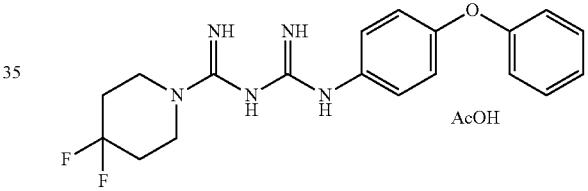

The title compound (0.32 g, 46.3%) in white solid was obtained according to the same method of Example 17, except that 4-phenoxyaniline was used.

1H NMR (600 MHz, DMSO-d6) δ 7.36 (m, 1H), 7.26 (s, 1H), 7.07 (m, 1H), 6.93 (m, 1H), 3.58 (m, 4H), 2.00 (m, 4H), 1.73 (s, 3H) LCMS 374.2 [M+H]⁺

Example 24. N—(N-(4-(trifluoromethoxy)carbamimidoyl)-4-ethoxypiperidine-1-carboximidamide acetate

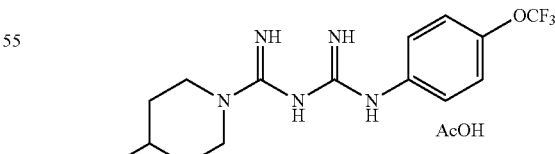

The title compound (0.10 g, 14.4%) in white solid was obtained according to the same method of Example 17, except that 4-ethoxypiperidine was used.

1H NMR (600 MHz, DMSO-d6) δ 7.43 (m, 2H), 7.22 (m, 2H), 3.72 (m, 2H), 3.52 (q, 2H), 3.17 (m, 2H), 1.85 (m, 2H), 1.82 (s, 3H), 1.45 (m, 2H), 1.11 (t, 3H) LCMS 374.2 [M+H]⁺

Example 25. N—(N-(4-(trifluoromethoxy)phenyl)carbamimidoyl)-3,3-difluoropyrrolidine-1-carboximidamide acetate

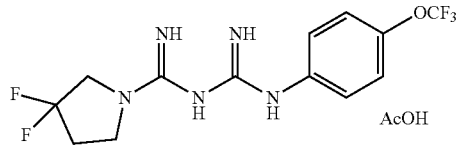 [SMILES: "AcOH" ; N=C(NC(=N)N1CCC(F)(F)C1)Nc1ccc(OC(F)(F)F)cc1]

The title compound (0.25 g, 36.7%) in white solid was obtained according to the same method of Example 17, except that 3,3-difluoropyrrolidine hydrochloride was used.

1H NMR (600 MHz, DMSO-d6) δ 7.36 (s, 2H), 7.23 (d, J=9.0 Hz, 2H), 7.78 (t, J=12.6 Hz, 2H), 2.57 (t, J=7.2 Hz, 2H), 2.47 (m, 2H), 1.75 (s, 3H)

LCMS 352.1 [M+H]$^+$

Example 26. N—(N-(3,4-dibromophenyl)carbamimidoyl)-4,4-difluoropiperidine-1-carboximidamide acetate

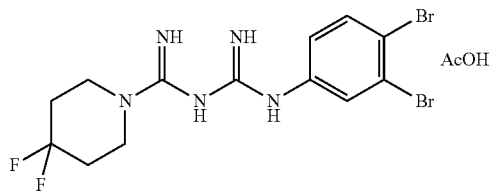 [SMILES: "AcOH" ; N=C(NC(=N)N1CCC(F)(F)CC1)Nc1ccc(Br)c(Br)c1]

The title compound (0.080 g, 14.0%) in white solid was obtained according to the same method of Example 17, except that 3,4-dibromoaniline was used.

1H NMR (600 MHz, DMSO-d6) δ 10.42 (s, 1H), 8.06 (s, 2H), 7.86 (m, 1H), 7.65 (d, J=8.4 Hz, 1H), 7.31 (m, 1H), 7.23 (s, 2H), 3.62 (s, 4H), 2.10 (s, 4H)

LCMS 440.1 [M+H]$^+$

Example 27. N—(N-(3-fluoro-4-(trifluoromethoxy)phenyl)carbamimidoyl)-4,4-fluoropiperidine-1-carboximidamide acetate

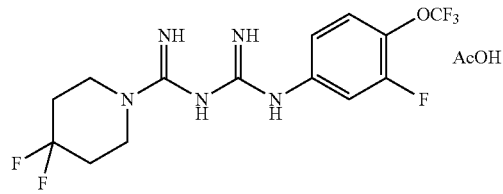 [SMILES: "AcOH" ; N=C(NC(=N)N1CCC(F)(F)CC1)Nc1ccc(OC(F)(F)F)c(F)c1]

The title compound (0.02 g, 8.2%) in white solid was obtained according to the same method of Example 17, except that 3-fluoro-4-trifluoromethoxyaniline was used.

1H NMR (600 MHz, DMSO-d6) δ 6.73 (m, 1H), 6.40 (m, 1H), 6.37 (m, 1H), 2.91 (s, 4H), 1.28 (s, 4H), 1.14 (s, 3H) LCMS 3842 [M+H]$^+$

Example 28. N—(N-(4-phenoxyphenyl)carbamimidoyl)-3,3-difluoropyrrolidine-1-carboximidamide acetate

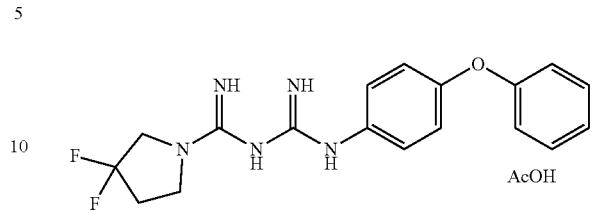

The title compound (0.20 g, 49.8%) in white solid was obtained according to the same method of Example 17, except that 3,3-difluoropyrrolidine hydrochloride and 4-phenoxyaniline were used.

1H NMR (600 MHz, DMSO-d6) δ 7.35 (m, 2H), 7.18 (m, 2H), 7.18 (brs, 2H), 7.07 (m, 2H), 6.94 (m, 2H), 3.76 (m, 2H), 3.56 (m, 2H), 2.46 (m, 2H), 1.76 (s, 3H) LCMS 360.0 [M+H]$^+$

Example 29. N—(N-(3-phenoxyphenyl)carbamimidoyl)-3,3-difluoropyrrolidine-1-carboximidamide acetate

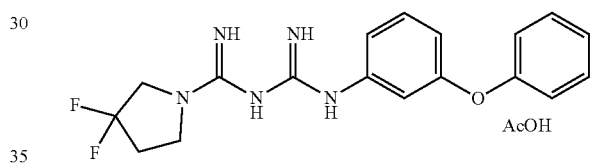

The title compound (0.36 g, 61.0%) in white solid was obtained according to the same method of Example 17, except that 3,3-difluoropyrrolidine hydrochloride and 3-phenoxyaniline were used.

1H NMR (600 MHz, DMSO-d6) δ 7.37 (t, J=7.8 Hz, 2H), 7.12 (m, 2H), 7.01 (m, 4H), 6.57 (m, 1H), 3.70 (t, J=7.2 Hz, 2H), 2.44 (m, 2H), 1.74 (s, 3H)

LCMS 360.0 [M+H]$^+$

Example 30. N—(N-(4-(trifluoromethyl)phenyl)carbamimidoyl)-3,3-difluoropyrrolidine-1-carboximidamide acetate

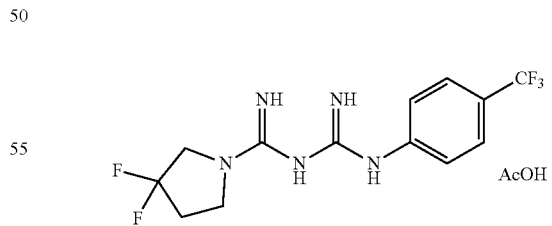

The title compound (0.21 g, 46.3%) in white solid was obtained according to the same method of Example 17, except that 3,3-difluoropyrrolidine hydrochloride and 4-trifluoromethylaniline was used.

1H NMR (600 MHz, DMSO-d6) δ 7.55 (m, 2H), 7.55 (m, 2H), 7.44 (brs, 2H), 3.79 (t, J=12.6 Hz, 2H), 3.58 (t, J=7.8 Hz, 2H), 2.48 (m, 2H), 1.77 (s, 3H)

LCMS 368.0 [M+H]$^+$

Example 31. N—(N-(3-chloro-4-iodophenyl)carbamimidoyl)-3,3-difluoropyrrolidine-1-carboximidamide acetate

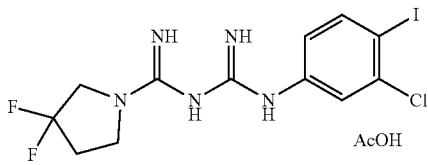 [SMILES: "AcOH" ; N=C(NC(=N)N1CCC(F)(F)C1)Nc1ccc(I)c(Cl)c1]

The title compound (0.06 g, 11.0%) in white solid was obtained according to the same method of Example 17, except that 3,3-difluoropiperidine hydrochloride and 3-chloro-4-iodoaniline was used.

1H NMR (600 MHz, DMSO-d6) δ 7.55 (m, 2H), 7.70 (m, 1H), 7.37 (brs, 1H), 6.87 (brs, 1H), 3.77 (t, J=13.2 Hz, 2H), 3.56 (t, J=7.2 Hz, 2H), 2.47 (m, 2H), 1.80 (s, 3H) LCMS 427.9 [M+H]+

Example 32. N—(N-(4-(trifluoromethythio)phenyl)carbamimidoyl)-3,3-difluoropyrrolidine-1-carboximidamide acetate

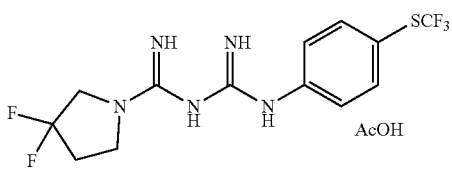

The title compound (0.04 g, 8.2%) in white solid was obtained according to the same method of Example 17, except that 3,3-difluoropiperidine hydrochloride and 3-trifluoromethythioaniline were used.

1H NMR (600 MHz, DMSO-d6) δ 7.55 (m, 2H), 7.35 (m, 2H), 3.79 (t, J=12.6 Hz, 2H), 3.58 (t, J=7.8 Hz, 2H), 2.48 (m, 2H), 1.80 (s, 3H)
LCMS 336.0 [M+H]+

Example 33. N—(N-(2-chlorophenyl)carbamimidoyl)-3,3-difluoropyrrolidine-1-carboximidamide acetate

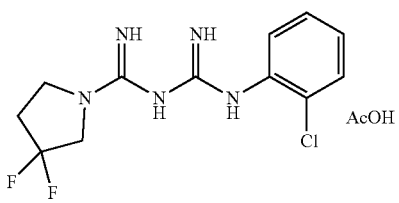 [SMILES: "AcOH" ; N=C(NC(=N)N1CCC(F)(F)C1)Nc1ccccc1Cl]

The title compound (0.09 g, 22.0%) in white solid was obtained according to the same method of Example 17, except that 3,3-difluoropiperidine hydrochloride and 2-chloroaniline were used.

1H NMR (600 MHz, DMSO-d6) δ 0.37 (dd, J=7.2 Hz, 1H), 7.20 (m, 1H), 7.06 (brs, 1H), 6.91 (m, 1H), 3.75 (t, J=13.2 Hz, 2H), 3.54 (t, J=7.8 Hz, 2H), 2.46 (m, 2H), 1.88 (s, 3H)
LCMS 302.0 [M+H]+

Example 34. N—(N-(2-bromophenyl)carbamimidoyl)-3,3-difluoropyrrolidine-1-carboximidamide acetate

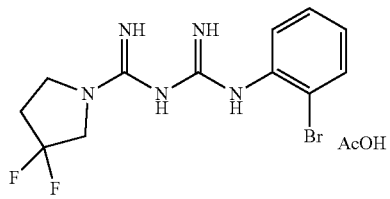 [SMILES: "AcOH" ; N=C(NC(=N)N1CCC(F)(F)C1)Nc1ccccc1Br]

The title compound (0.11 g, 24.6%) in white solid was obtained according to the same method of Example 17, except that 3,3-difluoro pyrrolidine hydrochloride and 2-bromoaniline were used.

1H NMR (600 MHz, DMSO-d6) δ 7.53 (dd, J=18 Hz, 1H), 7.22 (m, 1H), 7.00 (d, J=7.2 Hz, 1H), 6.88 (m, 1H), 3.76 (t, J=13.2 Hz, 2H), 3.55 (t, J=7.2 Hz, 2H), 2.45 (m, 2H), 1.88 (s, 3H) LCMS 345.9, 347.0 [M+H]+

Example 35. N—(N-(2,4-dichlorophenyl)carbamimidoyl)-3,3-difluoropyrrolidine-1-carboximidamide acetate

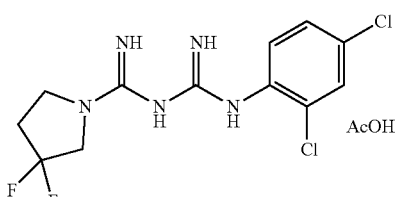

The title compound (0.10 g, 22.0%) in white solid was obtained according to the same method of Example 17, except that 3,3-difluoropiperidine hydrochloride and 2,4-dichloroaniline were used.

1H NMR (600 MHz, DMSO-d6) δ 7.42 (m, 1H), 7.21 (m, 2H), 7.0 (m, 1H), 3.68 (m, 2H), 3.54 (m, 2H), 2.42 (m, 2H), 1.89 (s, 3H)
LCMS 336.0, 337.9 [M+H]+

Example 36. N—(N-(2-propylphenyl)carbamimidoyl)-3,3-difluoropyrrolidine-1-carboximidamide acetate

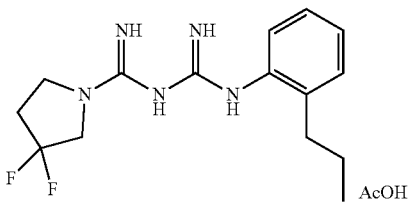 [SMILES: "AcOH" ; CCCc1ccccc1NC(=N)NC(=N)N1CCC(F)(F)C1]

The title compound (0.19 g, 45.0%) in white solid was obtained according to the same method of Example 17, except that 3,3-difluoro pyrrolidine hydrochloride and 2-propyl aniline was used.

1H NMR (600 MHz, DMSO-d6) δ 7.17 (m, 2H), 6.85 (m, 2H), 3.65 (m, 2H), 3.49 (s, 2H), 2.48 (m, 4H), 1.78 (s, 3H), 1.51 (m, 2H), 0.86 (s, 3H)
LCMS 310.1 [M+H]+

Example 37. N—(N-3,4-dimethoxyphenyl)carbamimidoyl)-3,3-difluoropyrrolidine-1-carboximidamide hydrochloride

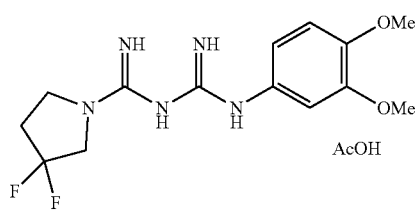 [SMILES: "AcOH" ; COc1ccc(NC(=N)NC(=N)N2CCC(F)(F)C2)cc1OC]

The title compound (0.16 g, 24.0%) in white solid was obtained according to the same method of Example 17, except that 3,3-difluoropyrrolidine hydrochloride and 3,4-dimethoxyaniline were used.
1H NMR (600 MHz, DMSO-d6) δ 6.41 (brs, 2H), 6.11 (d, J=18 Hz, 2H), 3.77 (t, J=12.6 Hz, 2H), 3.55 (s, 3H), 3.56 (t, J=6.6 Hz, 2H), 2.46 (m, 2H), 1.76 (s, 3H) LCMS 328.1 [M+H]+

Example 38. N—(N-(3-chloro-4-(trifluoromethoxy)phenyl)carbamimidoyl)-3,3-difluoropyrrolidine-1-carboximidamide acetate

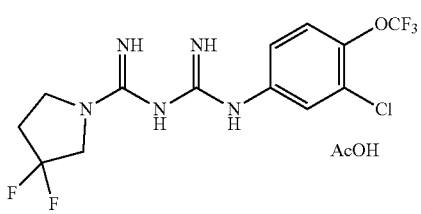 [SMILES: "AcOH" ; N=C(NC(=N)N1CCC(F)(F)C1)Nc1ccc(OC(F)(F)F)c(Cl)c1]

The title compound (0.06 g, 21.0%) in white solid was obtained according to the same method of Example 17, except that 3,3-difluoropyrrolidine hydrochloride and 3-chloro-4trifluoro methoxyaniline were used.
1H NMR (600 MHz, DMSO-d6) δ 7.36 (m, 2H), 7.19 (brs, 1H), 3.77 (t, J=13.8 Hz, 2H), 3.56 (m, 2H), 2.46 (m, 2H), 1.81 (s, 3H) LCMS 386.1 [M+H]+

Example 39 N—(N-(3-bromo-4-(trifluoromethoxy)phenyl)carbamimidoyl)-3,3-difluoropyrrolidine-1-carboximidamide acetate

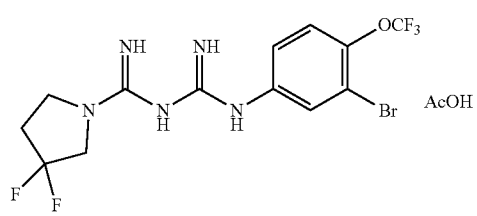 [SMILES: "AcOH" ; N=C(NC(=N)N1CCC(F)(F)C1)Nc1ccc(OC(F)(F)F)c(Br)c1]

The title compound (0.09 g, 11.0%) in white solid was obtained according to the same method of Example 17, except that 3,3-difluoropyrrolidine hydrochloride and 3-bromo-4-trifluoro methoxyaniline were used.
1H NMR (600 MHz, DMSO-d6) δ 7.51 (brs, 1H), 7.35 (d, J=8.4 Hz, 2H), 7.20 (brs, 2H), 3.78 (t, J=13.2 Hz, 2H), 3.37 (m, 2H), 2.46 (m, 2H), 1.80 (s, 3H) LCMS 432.0 [M+H]+

Example 40. N—(N-(2-bromobenzyl)carbamimidoyl)-4,4-difluoropiperidine-1-carboximidamide hydrochloride

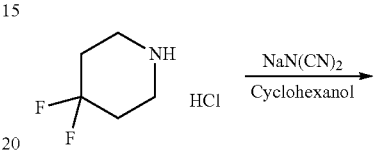

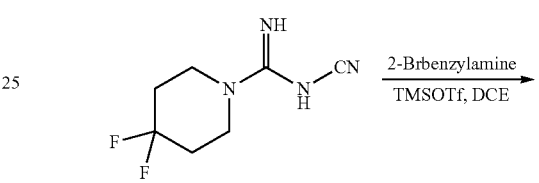

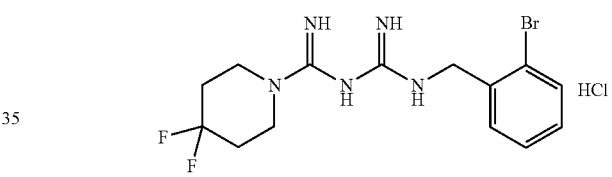

4,4-dichloropiperidine hydrochloride (1.0 g, 6.34 mmol) was dissolved in cyclohexanol (30 ml) at a room temperature and was added by sodium dicyanamide (0.62 g, 6.98 mmol). The solution was refluxed at 130° C. for 2 hours and cooled to a room temperature. By using ethylacetate and water, the aqueous layer was separated, dried under reduced pressure, and crystallized in a n-hexane to produce CN intermediate compound in a white solid (0.89 g, 75.2%). 2-bromobenzylamine (0.2 ml, 1.06 mmol) was dissolved in dichloroethane (2 mL) at a room temperature and was added by trimethylsilyltrifluoromethanesulfonate (0.23 ml, 1.27 mmol). The solution was agitated for 30 minutes at a room temperature, added by CN intermediate compound (0.21, 1.06 mmol) and refluxed for 15 hours at 80° C. After the reaction was completed, the solution was cooled to room temperature, and was agitated for 1 hour after addition of 12N hydrochloride (0.18 ml, 2.13 mmol). The produced solid was filtered, washed with dichloroethane (10 ml), dissolved in a small amount of methanol, and agitated for 1 hour at a room temperature after addition of ethylacetate 20 ml. The produced solid was filtered, washed with ethylacetate 10 ml and dried under vacuum to produce the title compound in white solid (0.25 g, 56.8%).

1H NMR (600 MHz, DMSO-d6) δ 7.69 (s, 1H), 7.62 (d, J=8.4 Hz, 1H), 7.45 (d, J=6.6 Hz, 1H), 7.40 (t, J=7.8 Hz, 1H), 7.24 (t, J=7.2 HZ, 1H), 7.11 (s, 2H), 4.40 (s, 2H), 3.54 (s, 4H), 2.09 (s, 4H) LCMS 374.1, 376.1 [M+H]+

Example 41. N—(N-(4-(trifluoromethoxy)benzyl)carbamimidoyl)-4,4-difluoropiperidine-1-carboximidamide hydrochloride

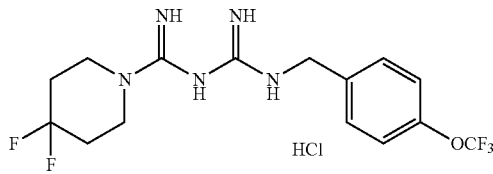 [SMILES: N=C(NCc1ccc(OC(F)(F)F)cc1)NC(=N)N1CCC(F)(F)CC1 ; Cl]

The title compound (0.22 g, 50.0%) in white solid was obtained according to the same method of Example 40, except that 4-trifluoromethoxybenzylamine was used.

1H NMR (600 MHz, DMSO-d6) δ 7.70 (s, 1H), 7.48 (s, 2H), 7.35 (d, J=7.8 Hz, 2H), 7.05 (s, 2H), 4.44 (s, 2H), 3.56 (s, 4H), 1.98 (s, 4H)

LCMS 380.4 [M+H]$^+$

Example 42. N—(N-(3,4-dichlorobenzyl)carbamimidoyl)-4,4-difluoropiperidine-1-carboximidamide hydrochloride

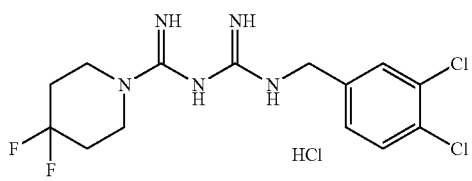 [SMILES: N=C(NCc1ccc(Cl)c(Cl)c1)NC(=N)N1CCC(F)(F)CC1 ; Cl]

The title compound (0.20 g, 46.5%) in white solid was obtained according to the same method of Example 40, except that 3,4-dichlorobenzylamine was used.

1H NMR (600 MHz, DMSO-d6) δ 7.62 (d, J=7.8 Hz, 2H), 7.35 (s, 1H), 7.03 (s, 3H), 4.38 (s, 2H), 3.56 (s, 4H), 2.08 (s, 4H) LCMS 364.1 [M+H]$^+$

Example 43. N—(N-(4-trifluoromethyl)benzyl)carbamimidoyl)-3,3-difluoropyrrolidine-1-carboximidamide hydrochloride

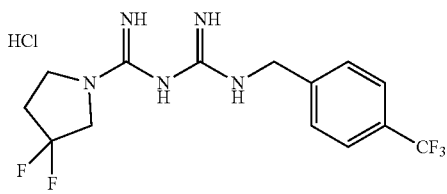 [SMILES: Cl ; N=C(NCc1ccc(C(F)(F)F)cc1)NC(=N)N1CCC(F)(F)C1]

The title compound (0.08 g, 12.0%) in white solid was obtained according to the same method of Example 40, except that 3,3-difluoropyrrolidine hydrochloride and 4-trifluoroemthylbenzylamine were used.

1H NMR (600 MHz, DMSO-d6) δ 7.69 (m, 2H), 7.51 (m, 2H), 4.42 (d, J=4.8 Hz, 2H), 3.67 (brs, 2H), 3.50 (m, 2H), 2.45 (m, 2H) LCMS: 350.1 [M+H]$^+$

Example 44. N—(N-(3-trifluoromethyl)benzyl)carbamimidoyl)-3,3-difluoropyrrolidine-1-carboximidamide hydrochloride

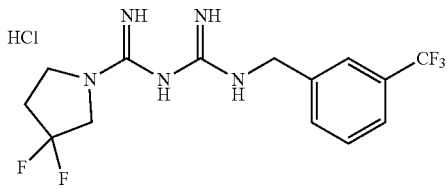 [SMILES: Cl ; N=C(NCc1cccc(C(F)(F)F)c1)NC(=N)N1CCC(F)(F)C1]

The title compound (0.12 g, 23.0%) in white solid was obtained according to the same method of Example 40, except that 3,3-difluoropyrrolidine hydrochloride and 3-trifluoroemthylbenzylamine were used.

1H NMR (600 MHz, CD3OD) δ 7.64 (m, 4H), 7.54 (m, 3H), 4.50 (s, 2H), 3.71 (brs, 2H), 3.62 (m, 2H) 2.46 (m, 2H) LCMS: 350.2 [M+H]$^+$

Example 45. N—(N-(3,4-dichloro)benzyl)carbamimidoyl)-3,3-difluoropyrrolidine-1-carboximidamide hydrochloride

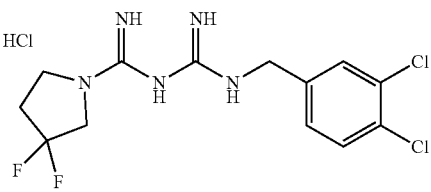 [SMILES: Cl ; N=C(NCc1ccc(Cl)c(Cl)c1)NC(=N)N1CCC(F)(F)C1]

The title compound (0.06 g, 10.0%) in white solid was obtained according to the same method of Example 40, except that 3,3-difluoropyrrolidine hydrochloride and 3,4-dichlorobenzylamine were used.

1H NMR (600 MHz, DMSO-d6) δ 8.01 (m, 1H), 7.58 (m, 2H), 7.47 (brs, 2H), 7.29 (m, 2H), 7.07 (brs, 2H), 4.33 (d, J=6.0 Hz, 2H), 3.70 (brs, 2H), 3.52 (brs, 2H), 2.48 (m, 2H) LCMS: 350.0, 352.0 [M+H]$^+$

Example 46. N—(N-phenethylcarbamimidoyl)-3,3-difluoropyrrolidine-1-carboximidamide hydrochloride

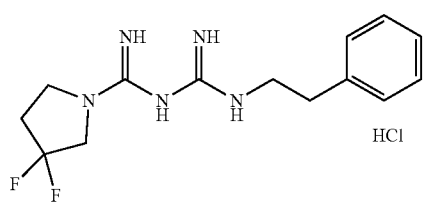 [SMILES: N=C(NCCc1ccccc1)NC(=N)N1CCC(F)(F)C1 ; Cl]

The title compound (0.12 g, 23.0%) in white solid was obtained according to the same method of Example 40, except that 3,3-difluoropyrrolidine hydrochloride and phenethylamine were used.

1H NMR (600 MHz, DMSO-d6) δ 7.33 (s, 1H), 7.25 (m, 5H), 3.75 (m, 2H), 3.57 (m, 2H), 3.34 (m, 2H), 2.78 (m, 2H), 2.49 (m, 2H) LCMS 266.1 [M+H]$^+$

Example 47. N—(N-(4-bromophenethyl)carbamimidoyl)-3,3-difluoropyrrolidine-1-carboximidamide hydrochloride

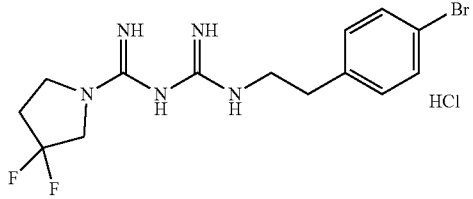 [SMILES: N=C(NCCc1ccc(Br)cc1)NC(=N)N1CCC(F)(F)C1 ; Cl]

The title compound (0.12 g, 25.0%) in white solid was obtained according to the same method of Example 40, except that 3,3-difluoropyrrolidine hydrochloride and 4-bromophenethylamine were used.

1H NMR (600 MHz, DMSO-d6) δ 7.48 (m, 2H), 7.24 (m, 2H), 3.78 (m, 2H), 3.57 (m, 2H), 3.35 (m, 2H), 2.76 (m, 2H), 2.49 (m, 2H) LCMS 374.0 376.0 [M+H]$^+$

Example 48. N—(N-(cyclopropylmethyl)carbamimidoyl)-4,4-difluoropiperidine-1-carboximidamide hydrochloride

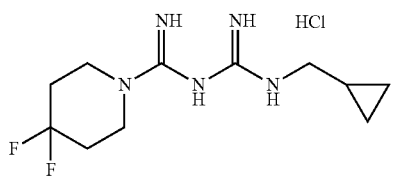 [SMILES: N=C(NCC1CC1)NC(=N)N1CCC(F)(F)CC1 ; Cl]

The title compound (0.67 g, 88.2%) in white solid was obtained according to the same method of Example 40, except that cyclopropylmethylamine was used.

1H NMR (600 MHz, DMSO-d6) δ 8.19 (s, 1H), 7.59 (s, 2H), 6.89 (s 1H), 3.59 (s, 4H), 3.12 (s, 2H) 1.98 (s, 4H), 0.99 (s, 2H), 0.45 (s, 2H), 0.21 (s, 2H) LCMS 260.1 [M+H]$^+$

Example 49. N—(N-cyclopropylcarbamimidoyl)-4,4-difluoropiperidine-1-carboximidamide hydrochloride

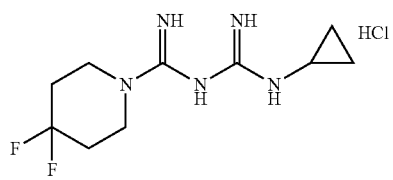 [SMILES: N=C(NC(=N)N1CCC(F)(F)CC1)NC1CC1 ; Cl]

The title compound (0.58 g, 88.0%) in white solid was obtained according to the same method of Example 40, except that cyclopropylamine was used.

1H NMR (600 MHz, DMSO-d6) δ 8.10 (s, 1H), 7.59 (s, 2H), 6.83 (s 1H), 3.31 (s, 4H), 3.22 (s, 4H), 1.88 (s, 4H), 1.12 (s, 4H) LCMS 246.1 [M+H]$^+$

Example 50. N—(N-cyclohexylcarbamimidoyl)-4,4-difluoropiperidine-1-carboximidamide hydrochloride

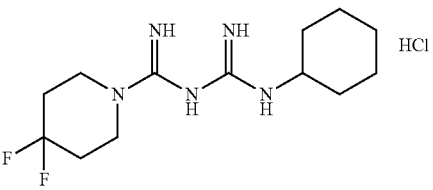 [SMILES: N=C(NC(=N)N1CCC(F)(F)CC1)NC1CCCCC1 ; Cl]

The title compound 0.25 g, 53.0%) in white solid was obtained according to the same method of Example 40, except that cyclohexylamine was used.

1H NMR (600 MHz, DMSO-d6) δ 8.19 (s, 1H), 7.34 (s, 2H), 7.00 (s, 2H), 3.81 (m, 4H), 3.63 (m, 1H), 3.31 (m, 2H), 2.99 (m, 2H), 2.30 (m, 4H), 2.20 (m, 4H), 1.02 (m, 2H) LCMS 288.0 [M+H]$^+$

Example 51. N—(N-(cyclopropylmethyl)carbamimidoyl)-3,3-difluoropyrrolidine-1-carboximidamide hydrochloride

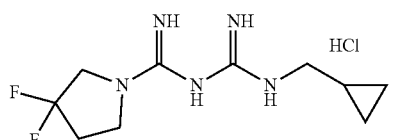

The title compound (0.50 g, 72.1%) in white solid was obtained according to the same method of Example 40, except that 3,3-difluoropyrrolidine hydrochloride and cyclopropylmethylamine were used.

1H NMR (600 MHz, DMSO-d6) δ 8.02 (s, 1H), 7.48 (s, 2H), 6.88 (s 1H), 3.31 (m, 4H), 3.31 (s, 2H), 2.00 (s, 2H), 1.01 (s, 1H) 0.45 (s, 2H), 0.21 (s, 2H) LCMS 246.0 [M+H]$^+$

Example 52. N—(N-(cyclopropylcarbamimidoyl)-3,3-difluoropyrrolidine-1-carboximidamide hydrochloride

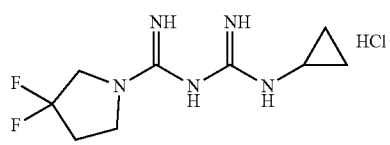 [SMILES: N=C(NC(=N)N1CCC(F)(F)C1)NC1CC1 ; Cl]

The title compound (0.72 g, 88.0%) in white solid was obtained according to the same method of Example 40, except that 3,3-difluoropyrrolidine hydrochloride and cyclopropylamine were used.

1H NMR (600 MHz, DMSO-d6) δ 8.12 (s, 1H), 7.58 (s, 2H), 6.78 (s 1H), 3.31 (m, 4H), 3.31 (s, 1H), 2.00 (s, 2H), 089 (s, 4H)

LCMS 232.0 [M+H]$^+$

Example 53. N—(N-(cyclohexylcarbamimidoyl)-3,3-difluoropyrrolidine-1-carboximidamide hydrochloride

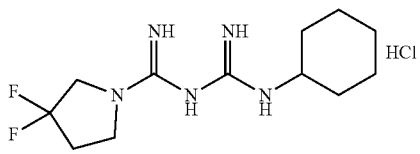 [SMILES: N=C(NC(=N)N1CCC(F)(F)C1)NC1CCCCC1 ; Cl]

The title compound (0.25 g, 55.3%) in white solid was obtained according to the same method of Example 40, except that 3,3-difluoropyrrolidine hydrochloride and cyclohexylamine were used.

1H NMR (600 MHz, DMSO-d6) δ 8.00 (s, 1H), 7.12 (s, 2H), 6.93 (s, 2H), 3.91 (m, 4H), 3.77 (m, 1H), 3.31 (m, 4H), 2.97 (m, 2H), 232 (m, 2H), 2.19 (m, 4H), 1.05 (m, 2H)

Example 54. N—(N-(3-bromobenzyl)carbamimidoyl)-4,4-difluoropiperidine-1-carboximidamide acetate

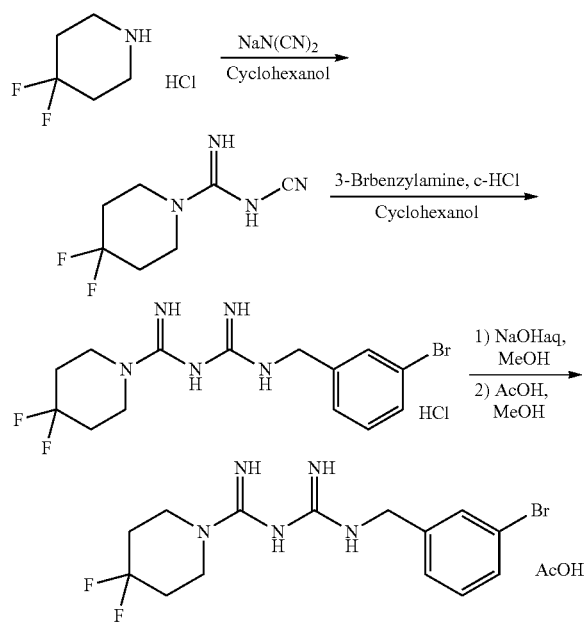

4,4-dichloropiperidine hydrochloride (1.0 g, 6.34 mmol) was dissolved in cyclohexanol (30 ml) at a room temperature and was added by sodium dicyanamide (0.62 g, 6.98 mmol). The solution was refluxed at 130° C. for 2 hours and cooled to a room temperature. By using ethylacetate and water, the aqueous layer was separated, dried under reduced pressure, and crystallized in a n-hexane to produce CN intermediate compound in a white solid (0.89 g, 75.2%). 3-bromobenzylamine (0.13 ml, 1.06 mmol) was dissolved in dichloroethane (10 mL) at a room temperature and was added by trimethylsilyltrifluoromethanesulfonate (0.23 ml, 1.28 mmol). The solution was agitated for 30 minutes at a room temperature, added by CN intermediate compound (0.20, 1.06 mmol) and refluxed for 15 hours at 80° C. After the reaction was completed, the solution was cooled to room temperature, and was agitated for 1 hour after addition of 12N hydrochloride (0.18 ml, 2.13 mmol). The produced solid was filtered, washed with dichloroethane (10 ml), dissolved in a small amount of methanol, and agitated for 1 hour at a room temperature after addition of 1.5M NaOH (0.5 ml). The produced solid was filtered, dissolved in methanol solution (10 ml) and agitated for 1 hour at room temperature after the addition of acetic acid solution (0.23 ml, 3.98 mmol). The reaction solution was distilled under vacuum and crystallized in ethylacetate to produce the title compound in white solid (0.16 g, 34.7%).

1H NMR (600 MHz, DMSO-d6) δ 7.59 (s, 1H), 7.46 (d, J=7.8 Hz, 1H), 7.30 (m, 1H), 4.33 (s, 2H), 3.52 (s, 4H), 3.34 (s, 3H), 1.97 (s, 4H)

LCMS 374.1, 376.1 [M+H]+

Example 55. N—(N-(4-bromobenzyl)carbamimidoyl)-4,4-difluoropiperidine-1-carboximidamide acetate

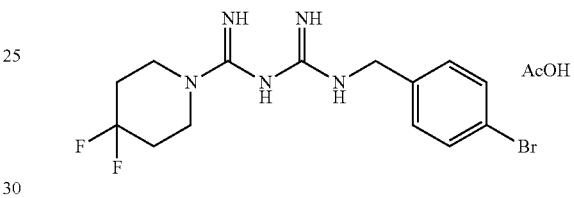

The title compound (0.02 g, 4.3%) in white solid was obtained according to the same method of Example 54, except that 4-bromobenzylamine was used.

1H NMR (600 MHz, DMSO-d6) δ 7.54 (d, J=8.4 Hz, 2H), 7.26 (d, J=7.8 Hz, 2H), 4.29 (s, 2H), 3.56 (s, 4H), 3.32 (s, 3H), 1.98 (s, 4H)

LCMS 374.1, 376.1 [M+H]+

Example 56. N—(N-(4-(trifluoromethoxy)phenyl)carbamimidoyl)-3,3-difluoropiperidine-1-carboximidamide hydrochloride

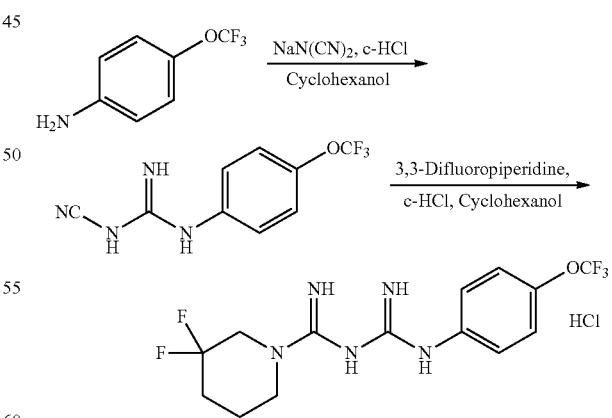

4-trifluoromethoxyaniline (2.0 g, 11.3 mmol) was dissolved in cyclohexanol (30 ml) at a room temperature and was added by sodium dicyanamide (1.1 g, 1.24 mmol). The solution was refluxed at 130° C. for 2 hours and cooled to a room temperature. By using ethylacetate and water, the aqueous layer was separated, dried under reduced pressure, and crystallized in a n-hexane to produce CN intermediate compound in a white solid (1.9 g, 10.0%).

3,3-difluoropiperidine (0.05 g, 0.41 mmol) was dissolved in dichloroethane (2 mL) at a room temperature and was added by trimethylsilyltrifluoromethanesulfonate (0.7 ml, 0.41 mmol). The solution was agitated for 30 minutes at a room temperature, added by CN intermediate compound (0.20, 1.06 mmol) and refluxed for 15 hours at 80° C. After the reaction was completed, the solution was cooled to room temperature, and was agitated for 1 hour after addition of 12N hydrochloride (0.34 ml, 0.41 mmol). The produced solid was filtered, washed with dichloroethane (10 ml), dissolved in a small amount of methanol, and agitated for 1 hour at a room temperature after addition of ethyl acetate 20 ml. The produced solid was filtered, washed with ethyl acetate 10 ml and dried under vacuum to produce the title compound in white solid (0.068 g, 41.0%).

1H NMR (600 MHz, DMSO-d6) δ 7.91 (m, 1H), 7.44 (m, 1H), 7.28 (m, 1H), 7.15 (m, 1H), 3.84 (t, J=12 Hz, 1H), 3.50 (m, 5H), 2.08 (m, 1H), 1.70 (m, 1H)

LCMS 366.1 [M+H]$^+$

Example 57. N—(N-(4-(trifluoromethoxy)phenyl)carbamimidoyl)thiazolidine-3-carboximidamide hydrochloride

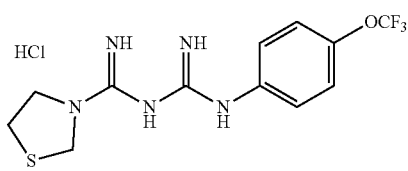 [SMILES: N=C(NC(=N)N1CCSC1)Nc1ccc(OC(F)(F)F)cc1 ; Cl]

The title compound (0.15 g, 33.3%) in white solid was obtained according to the same method of Example 56, except that thiazolidin was used.

1H NMR (600 MHz, DMSO-d6) δ 7.82 (m, 1H), 7.49 (m, 1H), 7.30 (d, J=18 Hz, 1H), 7.13 (m, 1H), 4.76 (brs, 2H), 4.47 (m, 1H), 3.64 (d, J=6.6 Hz, 1H), 3.12 (m, 1H), 1.70 (m, 1H) LCMS 334.0 [M+H]$^+$ Example 58. N—(N-(4-(trifluoromethoxy)phenyl)carbamimidoyl)-N-2,2-2-trifluoro ethylaminocarboximidamide hydrochloride

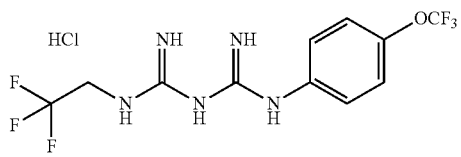 [SMILES: N=C(NCC(F)(F)F)NC(=N)Nc1ccc(OC(F)(F)F)cc1 ; Cl]

The title compound (0.16 g, 34.6%) in white solid was obtained according to the same method of Example 56, except 2,2,2-trifluoroethaneamine was used.

1H NMR (600 MHz, DMSO-d6) δ 8.27 (brs, 1H), 7.51 (m, 2H), 7.44 (m, 2H), 7.28 (m, 2H), 6.00 (brs, 3H), 4.00 (m, 2H)

LCMS 344.1 [M+H]$^+$

Example 59. N—(N-(4-(trifluoromethoxy)phenyl)carbamimidoyl)-4-(trifluoromethyl)piperidine-1-carboximidamide hydrochloride

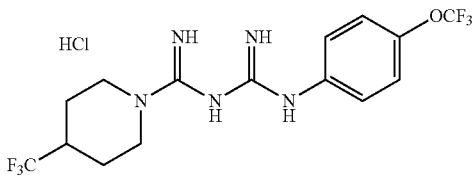 [SMILES: N=C(NC(=N)N1CCC(C(F)(F)F)CC1)Nc1ccc(OC(F)(F)F)cc1 ; Cl]

The title compound (0.04 g, 8.0%) in white solid was obtained according to the same method of Example 56, except 4-trifluoromethylpiperidine was used.

1H NMR (600 MHz, CD3OD) δ 7.46 (m, 2H), 7.25 (d, J=9.0 Hz, 2H), 7.29 (m, 1H), 7.21 (d, J=12.6 Hz, 1H), 3.05 (t, J=12.61 Hz, 2H), 2.54 (m, 1H), 1.95 (m, 2H), 1.60 (m, 2H)

LCMS 398.1 [M+H]$^+$

Example 60. N—(N-(4-(trifluoromethoxy)phenyl)carbamimidoyl)-N-1-cycloproylmethylaminocarboximidamide hydrochloride

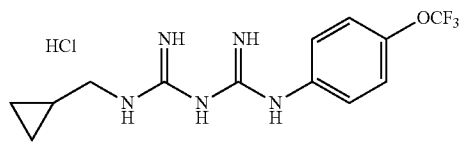 [SMILES: N=C(NCC1CC1)NC(=N)Nc1ccc(OC(F)(F)F)cc1 ; Cl]

The title compound (0.07 g, 29.3%) in white solid was obtained according to the same method of Example 56, except cyclopropylmethylamine was used.

1H NMR (600 MHz, DMSO-d6) δ 9.86 (brs, 1H), 7.84 (brs, 1H), 7.47 (m, 2H), 7.29 (m, 2H), 7.15 (brs, 1H), 2.99 (d, J=5.4 Hz, 2H), 1.16 (m, 1H), 0.44 (m, 2H) 0.22 (m, 2H) LCMS 316.11 [M+H]$^+$ Example 61. N—(N-(4-(trifluoromethoxy)phenyl)carbamimidoyl)-3,4,4-trifluoropiperidine-1-carboximidamide hydrochloride

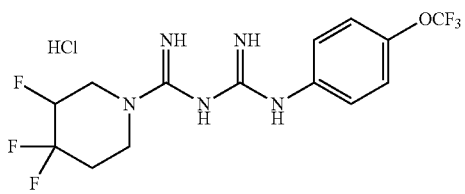 [SMILES: N=C(NC(=N)N1CCC(F)(F)C(F)C1)Nc1ccc(OC(F)(F)F)cc1 ; Cl]

The title compound (0.06 g, 25.1%) in white solid was obtained according to the same method of Example 56, except 3,4,4-trifluoropiperidine was used.

1H NMR (600 MHz, CD3OD) δ 7.43 (m, 2H), 7.25 (m, 2H), 4.82 (m, 2H), 4.39 (m, 1H), 4.05 (m, 1H), 3.56 (m, 1H), 2.27 (m, 1H), 2.13 (m, 1H)

LCMS 384.1 [M+H]$^+$

Example 62. N—(N-(4-(trifluoromethoxy)phenyl) carbamimidoyl)-4,4-difluoro-3-methylpiperidine-1-carboximidamide hydrochloride

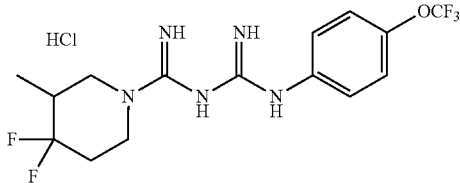 [SMILES: CC1CN(C(=N)NC(=N)Nc2ccc(OC(F)(F)F)cc2)CCC1(F)F ; Cl]

The title compound (0.07 g, 29.0%) in white solid was obtained according to the same method of Example 56, except 4,4-difluoro-3-methylpiperidine was used.

1H NMR (600 MHz, CD3OD) δ 7.43 (m, 2H), 7.25 (m, 2H), 3.95 (m, 2H), 3.34 (m, 1H), 3.06 (m, 1H), 2.15 (m, 1H), 1.99 (m, 1H), 1.03 (s, 3H)

LCMS 380.1 [M+H]$^+$

Example 63. N—(N-(4-(trifluoromethoxy)phenyl) carbamimidoyl)-4-fluoropiperidine-1-carboximidamide hydrochloride

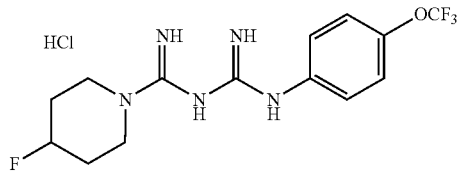 [SMILES: N=C(NC(=N)N1CCC(F)CC1)Nc1ccc(OC(F)(F)F)cc1 ; Cl]

The title compound (0.01 g, 4.4%) in white solid was obtained according to the same method of Example 56, except 4-fluoropiperidine was used.

1H NMR (600 MHz, CD3OD) δ 7.44 (m, 2H), 7.23 (m, 2H), 4.93 (m, 1H), 3.62 (m, 4H), 1.89 (m, 4H)

LCMS 348.1 [M+H]$^+$

Example 64. N—(N-(4-(trifluoromethoxy)phenyl) carbamimidoyl)-(R)-3-fluoropyrrolidin-1-carboximidamide hydrochloride

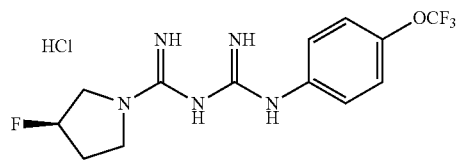 [SMILES: N=C(NC(=N)N1CC[C@@H](F)C1)Nc1ccc(OC(F)(F)F)cc1 ; Cl]

The title compound (0.12 g, 41.0%) in white solid was obtained according to the same method of Example 56, except (R)-3-fluoropyrrolidine was used.

1H NMR (600 MHz, CD3OD) δ 7.45 (d, J=9.0 Hz, 2H), 7.22 (d, J=9.0 Hz, 2H), 5.24 (m, 1H), 3.63 (m, 4H), 2.59 (m, 2H)

LCMS 334.1 [M+H]$^+$

Example 65. N—(N-(4-(trifluoromethoxy)phenyl) carbamimidoyl)-6-azaspiro[2.5]octane-6-carboximidamide hydrochloride

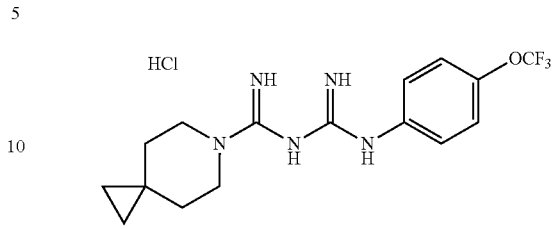

The title compound (0.02 g, 8.3%) in white solid was obtained according to the same method of Example 56, except 6-azaspiro[2.5]octane was used.

1H NMR (600 MHz, CD3OD) δ 7.45 (d, J=9.0 Hz, 2H), 7.22 (d, J=9.0 Hz, 2H), 3.60 (t, J=5.4 Hz, 4H), 1.47 (t, J=6.0 Hz, 4H), 1.47 (m, 4H)

LCMS 356.1 [M+H]$^+$

Example 66. N—(N-(4-(trifluoromethoxy)phenyl) carbamimidoyl)-3-azabicyclo[3.1.0]hexane-3-carboximidamide hydrochloride

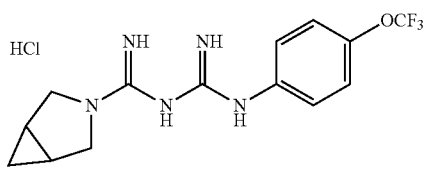 [SMILES: N=C(NC(=N)N1CC2CC2C1)Nc1ccc(OC(F)(F)F)cc1 ; Cl]

The title compound (0.16 g, 34.6%) in white solid was obtained according to the same method of Example 56, except 3-azabicyclo[3.1.0]hexane was used.

1H NMR (600 MHz, CD3OD) δ 7.45 (m, 2H), 7.22 (m, 2H), 3.69 (m, 1H), 3.54 (m, 3H), 3.31 (m, 1H), 1.74 (m, 1H), 0.84 (m, 1H), 0.21 (m, 1H)

LCMS 328.1 [M+H]$^+$

Example 67. N-carbamimidoyl-3,3-difluoropyrrolidine-1-carboximidamide hydrochloride

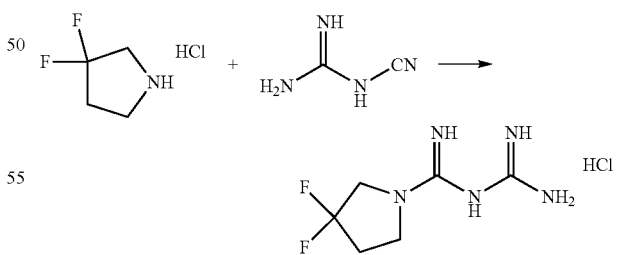

3,3-difluoropyrrolidine (0.03 g, 0.21 mmol) and dicyandiamide (0.019 g, 0.23 mmol) were added and agitated for 2 hours at 110° C. After the reaction was completed, the solution was cooled to room temperature, and was added by methanol. The solution was added by ethylacetate to obtain the solid. The solid was filtrated, washed with ethyl acetate, and dried under vacuum to produce the title compound in white solid (0.02 g, 58.0%).

1H NMR (600 MHz, DMSO) δ 7.37 (s, 2H), 7.02 (s, 3H), 3.78 (m, 2H), 3.57 (m, 4H) LCMS 191.1 [M+H]+

Example 68. N-carbamimidoyl-4,4-difluoropiperidine-1-carboximidamide hydrochloride

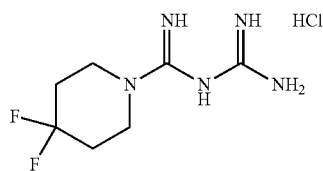 [SMILES: Cl ; N=C(N)NC(=N)N1CCC(F)(F)CC1]

The title compound (0.02 g, 60.0%) in white solid was obtained according to the same method of Example 67, except that 4,4-difluoropiperidine hydrochloride was used.
1H NMR (600 MHz, CD3OD) δ 3.69 (m, 4H), 2.06 (m, 4H)
LCMS: 206.1 [M+H]+

Example 69. N-((4,4-difluoropiperidin-1-yl)(imino)methyl)-4,4-difluoro piperidine-1-carboximidamide hydrochloride

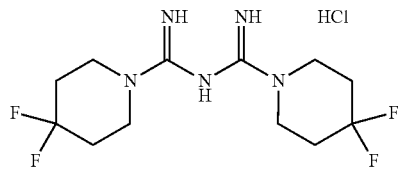 [SMILES: Cl ; N=C(NC(=N)N1CCC(F)(F)CC1)N1CCC(F)(F)CC1]

The title compound (0.03 g, 40.0%) in white solid was obtained according to the same method of Example 67, except that 4,4-difluoropiperidine hydrochloride was used.
1H NMR (600 MHz, CD3OD) δ 3.65 (m, 8H), 1.99 (m, 8H) LCMS: 310.1 [M+H]+

Test Example 1: Test for Inhibition of OCR and Enhancement of ECAR

A549 cells were purchased from American Type Tissue Culture Collection (CCL-185™) and cultured in RPMI 1640 supplied with 10% fetal bovine serum (FBS) and antibiotic-antimycotic (Lifetech, CA). A549 cells were separated with 0.5% Trypsin-EDTA and 3,000 cells were plated on 1 mg/ml poly-D-lysine (Sigma, P6407) coated XF 96 well culture media. A549 cells were allowed to adhere to the wells for 24 hours under the condition of temperature, 37° C. and 5% $CO_2$. The sensor cartridge of XF Analyzer was soaked in 200 μl of Calibrant solution (Seahorse, MA) in a clear 96-well plate at 37° C. for 24 hours. The compounds of the present invention were diluted with RPMI 1640 without FBS, transferred to A549 cells on XF 96 well plate, and incubated further for 23 hours at 37° C. and 5% $CO_2$. After incubation, the compound solution was exchanged with pre-warmed and pH adjusted (pH7.4) XF assay media (Seahorse) supplied with 15 mM D-glucose (Sigma), 15 mM sodium pyruvate (Lifetechnologies, CA) and 4 mM L-glutamine (Lifetechnologies, CA). The compounds of present invention were prepared in XF Assay media and added to the assay plate. The assay plate was equilibrated in XF Analyzer for 1 hour, and the reading were started by sensor cartridge. The cytotoxicity assay was followed using Cyquant (Lifetechnologies, CA) in order to calibrate the inhibition with cytotoxicity of compounds. The concentrations of the compounds were tested at 0, 0.5, 1, 5, 10 and 20 μM and IC50 value was obtained from the inhibited values. That is, from OCR inhibition values at each concentration of the compound, IC50 was calculated according to Prism's dose response curve fitting.

In Table 1, the levels of OCR IC50 are evaluated by the following.
A Level: IC50<2 uM
B Level: IC50=2~4 uM
C Level: IC50>4 uM According to the test results of the compounds, the compounds were classified into A, B and C. The test results are summarized in Table 1. The test compounds had good OCR inhibitory effect, which suggested the excellent OXPHOX inhibitor. The most compounds having an OCR inhibitory activity showed the increased ECAR.

TABLE 1

| Example No. | OCR IC50 (A549, 24 hrs) | ECAR Enhancement (A549, 24 hrs) |
|---|---|---|
| 2 | C | No test |
| 3 | C | No test |
| 5 | C | No test |
| 6 | C | No test |
| 8 | C | No test |
| 9 | B | No test |
| 10 | C | No test |
| 11 | C | No test |
| 13 | B | No test |
| 14 | B | No test |
| 17 | B | No test |
| 18 | B | No test |
| 21 | B | + |
| 22 | B | + |
| 23 | B | + |
| 25 | B | + |
| 26 | B | No test |
| 27 | A | + |
| 28 | B | No test |
| 29 | A | + |
| 30 | B | + |
| 31 | B | No test |
| 32 | B | + |
| 38 | B | + |
| 39 | B | No test |
| 40 | C | No test |
| 42 | C | No test |
| 55 | C | No test |

Test Example 2: Cytotoxicity in Low Glucose Condition

SK-MEL-28 (HTB-72) is a melanoma cell line obtained from ATCC (MA) and cultured in RPMI 1640 media (Lifetechnologies, CA) with supplement of 10% FBS and antibiotic-antimycotic (Lifetechnologies, CA). RPMI 1640 (−Glucose) was used to prepare low glucose media and 0.75 mM glucose was supplied with D-(+)-glucose solution from Sigma. SK-MEL-28 cells were separated from culture plate using 0.5% trypsin-EDTA and 1,250 cells were plated in 96-well plate with low glucose media. After incubation at 37° C. for 24 hour, 5% $CO_2$, the cells were treated with the compounds of present invention in FBS-free media for 72 hours. The cytotoxicity was measured by the MTT (AM-RESCO, OH) assay. NADH-dependent cellular oxidoreductase reduces MTT to its insoluble tetrazolium with purple color. The enzyme depends on cell number or energy state of cells. 10 µl of 5 mg/ml MTT solution was added to each well of the assay plate and skip the well for blank. The plate was incubated at 37° C. and 5% $CO_2$ for 2 hours. The MTT solution was removed from each well and 100 µl of DMSO was added. The plate was read by VICTOR X3 Multilabel Counter at the wavelength of 550 nm. In Table 2, the levels of IC50 are evaluated by the following criteria.

A Level: IC50<6 uM
B Level: IC50=6~15 uM
C Level: IC50>15 uM

According to the concentration of compound for killing the half of cell populations (the levels of IC50), the compounds were classified into A, B and C, when the compounds were treated on SK-MEL-28 cells at 0.75 mM glucose. The test result is summarized in Table 1. The test compounds have good cell death effect at a low concentration, and thus are suggested to show excellent anti-cancer activity.

TABLE 2

| Example No. | SK-MEL-28 0.75 mM glucose cell viability (IC50 µM) |
|---|---|
| 1 | C |
| 2 | B |
| 3 | A |
| 4 | C |
| 5 | B |
| 6 | B |
| 8 | B |
| 9 | A |
| 10 | B |
| 11 | B |
| 13 | A |
| 14 | A |
| 21 | A |
| 22 | A |
| 22 | B |
| 23 | A |
| 25 | A |
| 26 | B |
| 27 | A |
| 28 | A |
| 29 | A |
| 30 | B |
| 31 | B |
| 32 | A |
| 38 | B |
| 42 | B |

Test Example 3: In Vitro Combination Study

A549, H1975 (CRL5908, ATCC) or U937 cell (CRL1593.2™, ATCC) lines were cultured in RPMI 1640 media (Lifetechnologies, CA) with supplement of 10% FBS and antibiotic-antimycotic (Lifetechnologies, CA). Dasatinib (Combi-Blocks, San Diego, Calif.) is Bcr-Abl-tyrosine kinase inhibitor and Src family tyrosine kinase inhibitor approved for CML treatment. GDC094 (Selleckchem, Houston, Tex.) is a pan-PI3K inhibitor and effective in various cancer cells. H1975 or A549 cells were dissociated from culture plate using 0.5% trypsin-EDTA (Lifetechnologies, CA) and were suspended. U937 cells were spun down using centrifugation. A549 cells were seeded at a density of 3,000 cells/well and H1975 or U937 cells were seeded at a density of 5,000 cells/well in a 96-well plate, and were allowed to adhere at 37° C. and 5% $CO_2$ for 24 hours. $IC_{50}$ of each compounds were obtained from each cell line prior to the combination therapy test. Among four concentrations of the compounds of present invention, the highest concentration was set to $IC_{80}$ and the lowest concentration was approximately $IC_{30}$. The concentrations of other anticancer drug were ranged from $IC_{80}$ to $IC_{30}$. The media in 96-well plate were exchanged with the prepared compound solution. To determine cell viability, except U937 cells, 10 µl of 5 mg/ml MTT in D-PBS (Lifetechnologies, CA) were added to each well after 72-hour treatment and plates were incubated at 37° C. and 5% CO2 for 2 hours. 100 µl of DMSO was added after removing MTT solution from each well, and were read by VICTOR X3 Multilabel Counter at the wavelength of 550 nm. The combination index was calculated using Calcusyn (Biosoft, UK).

Test Example 4: In Vivo Testing OXPHOS Inhibitors for Anticancer Activity

The SK-MEL-239 tumor cell line was maintained in vitro as monolayer in RPMI1 640 medium supplemented with 10% heat inactivated fetal bovine serum, 100 U/ml penicillin and 100 µg/ml streptomycin, and L-glutamine (2 mM) at 37° C. in an atmosphere of 5% $CO_2$ in air. The tumor cells were routinely subcultured twice weekly with 0.5% trypsin-EDTA treatment. The cells growing in an exponential growth phase were harvested and counted for tumor cell inoculation.

Female BALB/c nude mice aged 6-8 weeks and weighing approximately 18-22 g were purchased from Vital River. Each mouse was inoculated subcutaneously at the right flank with SK-MEL-239 tumor cells ($1 \times 10^7$) in 0.1 ml of PBS for tumor development. The treatment was started, when the tumor size reaches approximately 100 $mm^3$.

100 mg/kg of Phenformin and 15 mg/kg of Vemurafenib were administered via oral gavage twice daily and 100 mg/kg HLPO1 (HL176001001) was administered once daily for 21 days. Tumor volumes were measured twice a week in two dimensions using a caliper, and the volume was expressed in $mm^3$ using the formula: $V=0.5 \times a \times b^2$, where a and b were the long and short diameters of the tumor, respectively. The T/C value (in percentage) was an indication of antitumor effect. T and C were the mean volumes of the treated and control groups, respectively.

The invention claimed is:

1. A compound having Chemical Formula 1, or a pharmaceutically acceptable salt thereof:

[Chemical Formula 1]

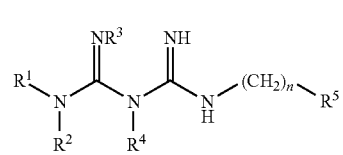

wherein $R^1$ and $R^2$ are taken together with N to which they are attached to form a pyrrolidine group and is substituted with at least a group selected from the group consisting of halogen, $C_1$-$C_4$ alkyl, $C_1$-$C_4$ haloalkyl, $C_1$-$C_4$ alkoxy, and $C_1$-$C_2$ alkylamino, $R^3$ and $R^4$ are H,
n is 0, 1 or 2, and
$R^5$ is an aryl group represented by Chemical Formula 2,

[Chemical Formula 2]

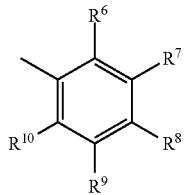

wherein $R^6$, $R^7$, $R^8$, $R^9$, and $R^{10}$ are independently $SR^{11}$ where $R^{11}$ is $C_1$-$C_3$ alkyl, $C_1$-$C_3$ haloalkyl, or $C_6$-$C_{10}$ aryl, wherein only one of $R^6$, $R^7$, $R^8$, $R^9$, and $R^{10}$ is $SR^{11}$ with the other positions being H or $OR^{12}$, where $R^{12}$ is a is $C_1$-$C_3$ alkyl, $C_6$-$C_{10}$ aryl, wherein up to three of $R^6$, $R^7$, $R^8$, $R^9$, and $R^{10}$ are $OR^{12}$ with the other positions being H.

2. The compound of claim 1, wherein, in Chemical Formula 1, $R^1$ and $R^2$ are taken together with N to which they are attached to form a pyrrolidine group and is substituted with at least one halogen,
$R^3$ and $R^4$ are H,
n is 0, 1, or 2, and
$R^5$ is aryl group represented by Chemical Formula 2 where $R^6$, $R^7$, $R^8$, $R^9$, and $R^{10}$ are independently $SR^{11}$ where $R^{11}$ is $C_1$-$C_3$ alkyl, $C_1$-$C_3$ haloalkyl, or $C_6$-$C_{10}$ aryl, wherein only one of $R^6$, $R^7$, $R^8$, $R^9$, and $R^{10}$ is $SR^{11}$ with the other positions being H, or $OR^{12}$, where $R^{12}$ is a is $C_1$-$C_3$ alkyl, $C_6$-$C_{10}$ aryl, wherein up to three of $R^6$, $R^7$, $R^8$, $R^9$, and $R^{10}$ are $OR^{12}$ with the other positions being H.

3. A compound selected from the group consisting of the following compounds, or a pharmaceutically acceptable salt thereof:
N—(N-(4-(trifluoromethoxy)phenyl)carbamimidoyl)-3,3-difluoropyrrolidine-1-carboximidamide,
N—(N-(4-phenoxyphenyl)carbamimidoyl)-3,3-difluoropyrrolidine-1-carboximidamide,
N—(N-(3-phenoxyphenyl)carbamimidoyl)-3,3-difluoropyrrolidine-1-carboximidamide,
N—(N-(4-(trifluoromethyl)phenyl)carbamimidoyl)-3,3-difluoropyrrolidine-1-carboximidamide,
N—(N-(3-chloro-4-iodophenyl)carbamimidoyl)-3,3-difluoropyrrolidine-1-carboximidamide,
N—(N-(4-(trifluoromethylthio)phenyl)carbamimidoyl)-3,3-difluoropyrrolidine-1-carboximidamide,
N—(N-(2-chlorophenyl)carbamimidoyl)-3,3-difluoropyrrolidine-1-carboximidamide,
N—(N-(2-bromophenyl)carbamimidoyl)-3,3-difluoropyrrolidine-1-carboximidamide,
N—(N-(2,4-dichlorophenyl)carbamimidoyl)-3,3-difluoropyrrolidine-1-carboximidamide,
N—(N-(2-propylphenyl)carbamimidoyl)-3,3-difluoropyrrolidine-1-carboximidamide,
N—(N-(3,4-dimethoxyphenyl)carbamimidoyl)-3,3-difluoropyrrolidine-1-carboximidamide,
N—(N-(3-chloro-4-(trifluoromethoxy)phenyl)carbamimidoyl)-3,3-difluoropyrrolidine-1-carboximidamide,
N—(N-(3-bromo-4-(trifluoromethoxy)phenyl)carbamimidoyl)-3,3-difluoropyrrolidine-1-carboximidamide,
N—(N-(4-(trifluoromethyl)benzyl)carbamimidoyl)-3,3-difluoropyrrolidine-1-carboximidamide,
N—(N-(3-(trifluoromethyl)benzyl)carbamimidoyl)-3,3-difluoropyrrolidine-1-carboximidamide,
N—(N-(3,4-(dichloro)benzyl)carbamimidoyl)-3,3-difluoropyrrolidine-1-carboximidamide,
N—(N-phenethylcarbamimidoyl)-3,3-difluoropyrrolidine-1-carboximidamide,
N—(N-(4-bromophenethyl)carbamimidoyl)-3,3-difluoropyrrolidine-1-carboximidamide,
N—(N-(cyclopropylmethyl)carbamimidoyl)-3,3-difluoropyrrolidine-1-carboximidamide,
N—(N-(cyclopropyl)carbamimidoyl)-3,3-difluoropyrrolidine-1-carboximidamide,
N—(N-(cyclohexyl)carbamimidoyl)-3,3-difluoropyrrolidine-1-carboximidamide, and
N—(N-(4-(trifluoromethoxy)phenyl)carbamimidoyl)-(R)-3-fluoropyrrolidine-1-carboximidamide.

4. A pharmaceutical composition comprising the compound or the pharmaceutically acceptable salt thereof of claim 1 as an active ingredient, and a pharmaceutically acceptable carrier.

5. The pharmaceutical composition of claim 4, wherein the pharmaceutical composition is formulated as a tablet, a capsule, a pill, a granule, powder, an injection or a liquid.

* * * * *